(12) United States Patent
Qin et al.

(10) Patent No.: US 7,575,882 B2
(45) Date of Patent: Aug. 18, 2009

(54) COMPOSITIONS AND METHODS FOR IDENTIFYING MODULATORS OF TRPV2

(75) Inventors: Ning Qin, Blue Bell, PA (US); Yi Liu, Jenkintown, PA (US); Christopher M. Flores, Lansdale, PA (US); Tasha Hutchinson, Green Lane, PA (US); Michael P. Neeper, Collegeville, PA (US)

(73) Assignee: Janssen Pharmaceutica N. V., Beerse (BE)

( * ) Notice: Subject to any disclaimer, the term of this patent is extended or adjusted under 35 U.S.C. 154(b) by 186 days.

(21) Appl. No.: 11/589,340

(22) Filed: Oct. 30, 2006

(65) Prior Publication Data

US 2007/0105086 A1 May 10, 2007

Related U.S. Application Data

(60) Provisional application No. 60/731,686, filed on Oct. 31, 2005, provisional application No. 60/782,656, filed on Mar. 15, 2006.

(51) Int. Cl.
*G01N 33/567* (2006.01)
*C07K 14/705* (2006.01)

(52) U.S. Cl. .................................... 435/7.21; 435/7.2
(58) Field of Classification Search ....................... None
See application file for complete search history.

(56) References Cited

FOREIGN PATENT DOCUMENTS

| GB | 2346882 A | 8/2000 |
|----|-----------|--------|
| WO | WO 99/37675 A | 7/1999 |
| WO | WO 02/069993 A1 | 9/2002 |
| WO | WO 2005/089206 A | 9/2005 |
| WO | WO 2006/005471 A | 1/2006 |
| WO | WO 2006/116703 A | 11/2006 |

OTHER PUBLICATIONS

Hohmann A.G. et al.: "Cannabinoid Suppression of Noxious Heat-Evoked Activity in Wide Dynamic Range Neurons in the Lumbar Dorsal Horn of the Rat" Journal of Neurophysiology Feb. 1999, vol. 81, No. 2, pp. 575-583, XP002423708.
International Search Report dated Mar. 23, 2007 for Appln. No. PCT/US2006/042241.

*Primary Examiner*—John D Ulm
(74) *Attorney, Agent, or Firm*—Laura Donnelly

(57) ABSTRACT

It has now been discovered that certain cannabinoids specifically activate TRPV2 channel activity. Based on the discovery, novel compositions and methods for screening, identifying and characterizing compounds that increase or decrease the biological activity of a TRPV2.

18 Claims, 7 Drawing Sheets

Figure 1

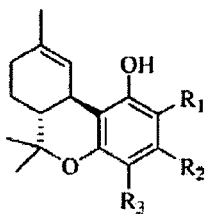

Δ⁹-Tetrahydrocannabinols (THCs)

$R_1$ or $R_3$ = H or COOH
$R_2$ = $C_1$, $C_3$, $C_4$, $C_5$ side chain

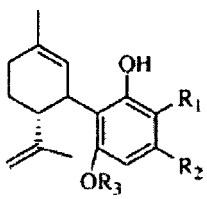

Cannabidiols (CBDs)

$R_1$ = H or COOH
$R_2$ = $C_1$, $C_3$, $C_4$, $C_5$ side chain
$R_3$ = H or $CH_3$

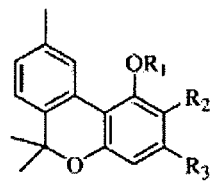

Cannabinols (CBNs)

$R_1$ = H or $CH_3$
$R_2$ = H or COOH
$R_3$ = $C_1$, $C_3$, $C_4$, $C_5$ side chain

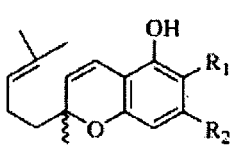

Cannabichromenes (CBCs)

$R_1$ = H or COOH
$R_2$ = $C_3$, $C_5$ side chain

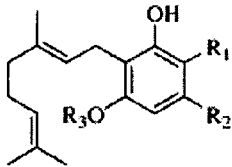

Cannabigerols (CBGs)

$R_1$ = H or COOH
$R_2$ = $C_3$, $C_5$
$R_3$ = H, $CH_3$

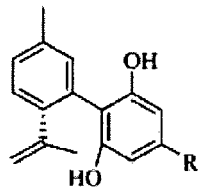

Cannabinodiols (CBNDs)

R = $C_3$, $C_5$ side chain

Figure 3
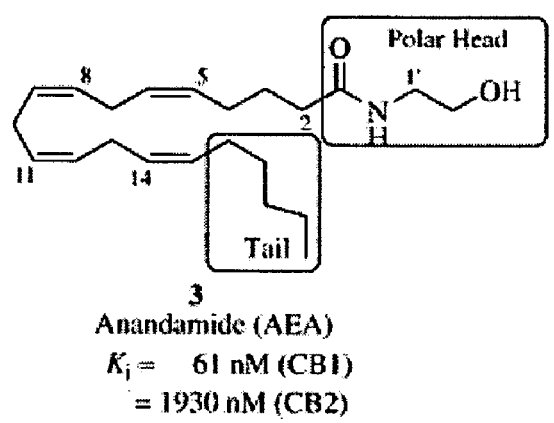
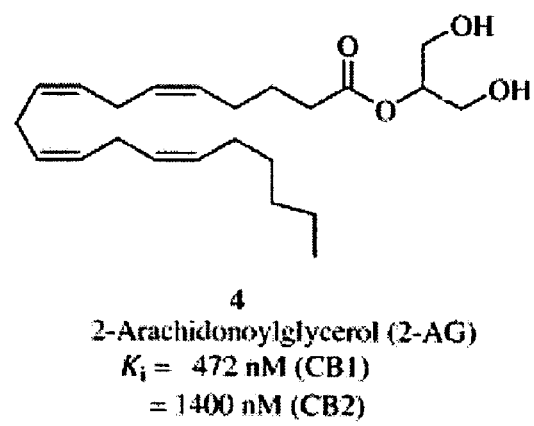
3
Anandamide (AEA)
$K_i$ = 61 nM (CB1)
    = 1930 nM (CB2)
4
2-Arachidonoylglycerol (2-AG)
$K_i$ = 472 nM (CB1)
    = 1400 nM (CB2)

Figure 4
A.
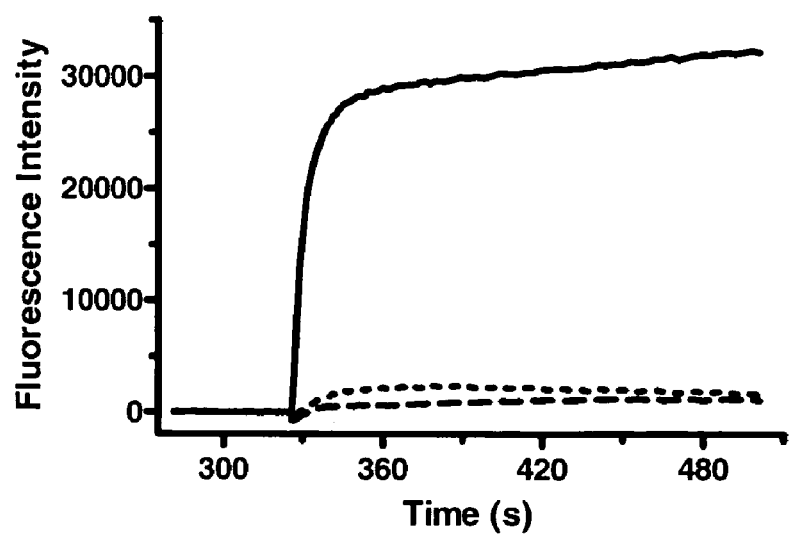
B.
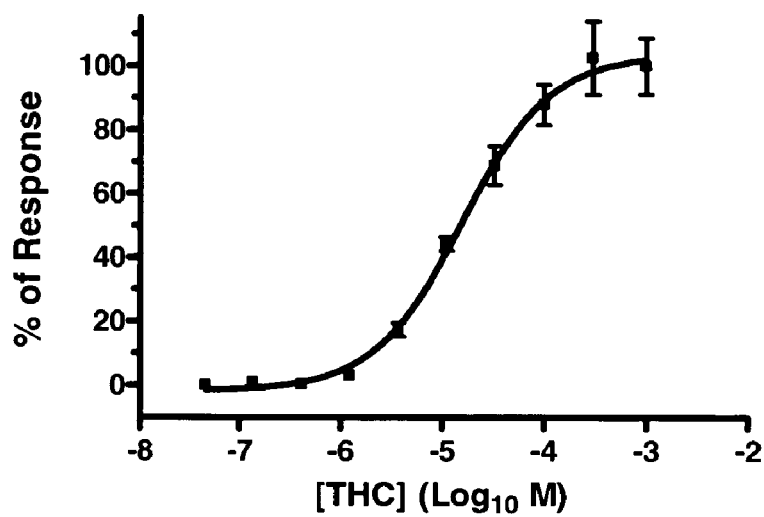

Figure 5
A.
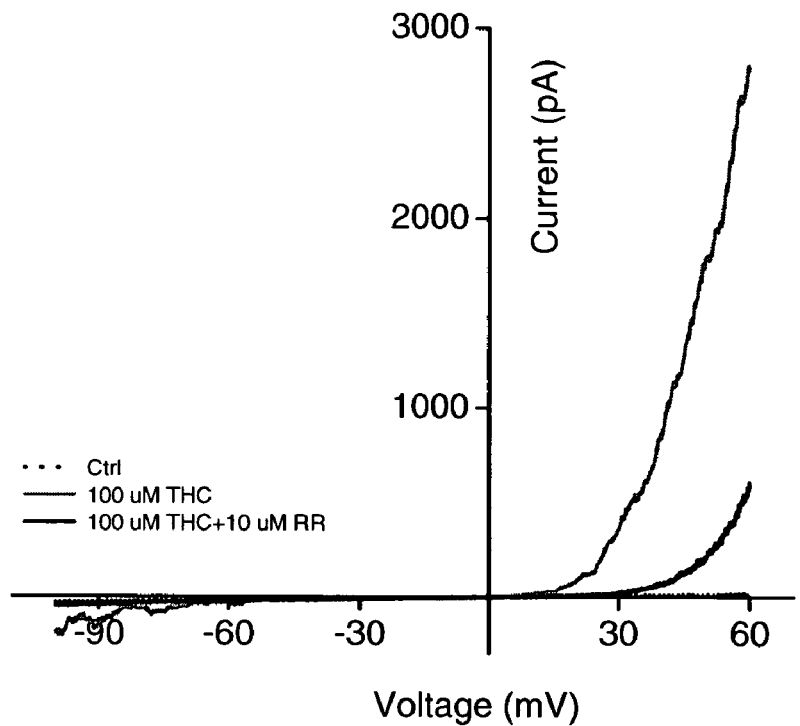
B.
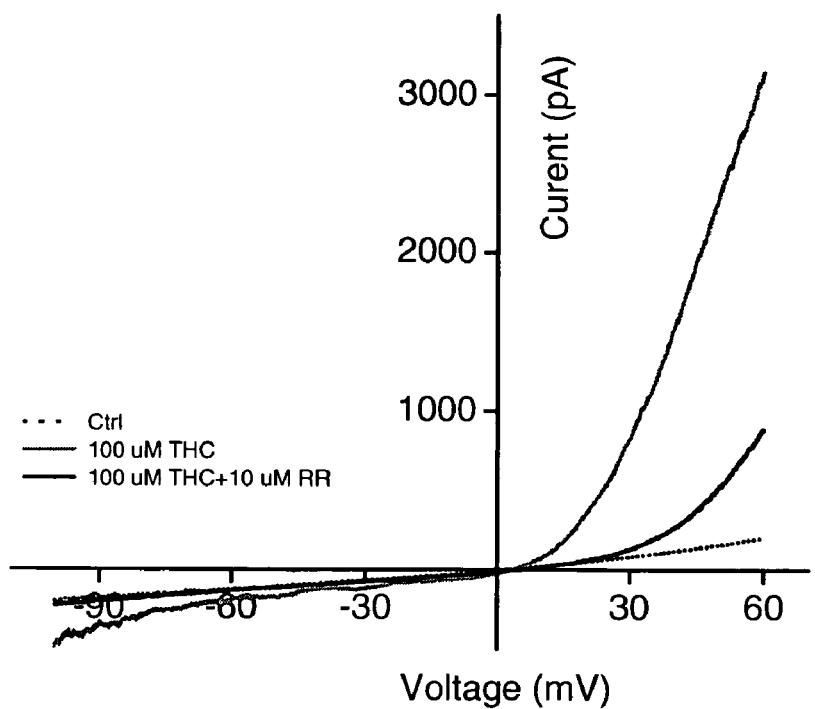

Figure 6
A.
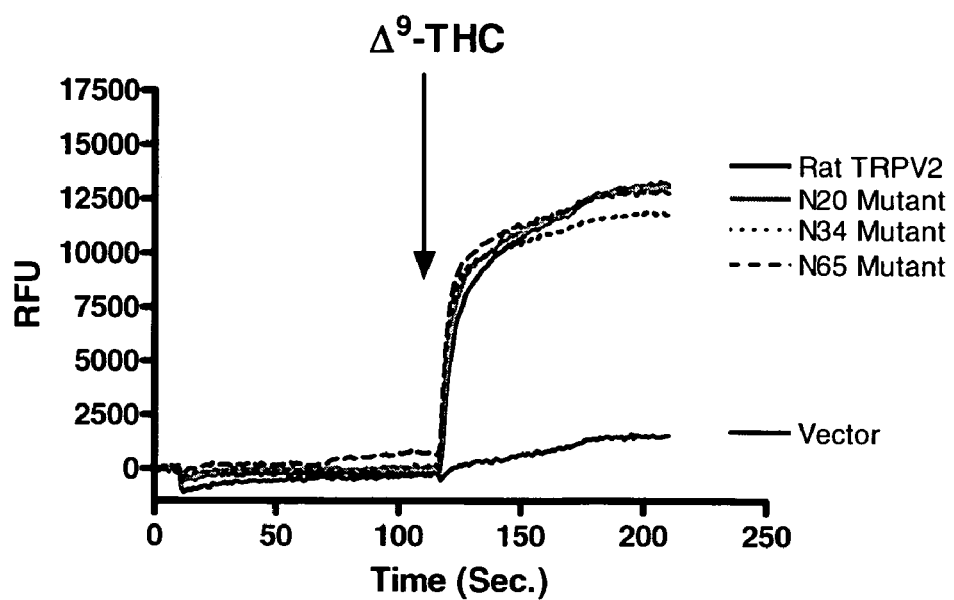
B.
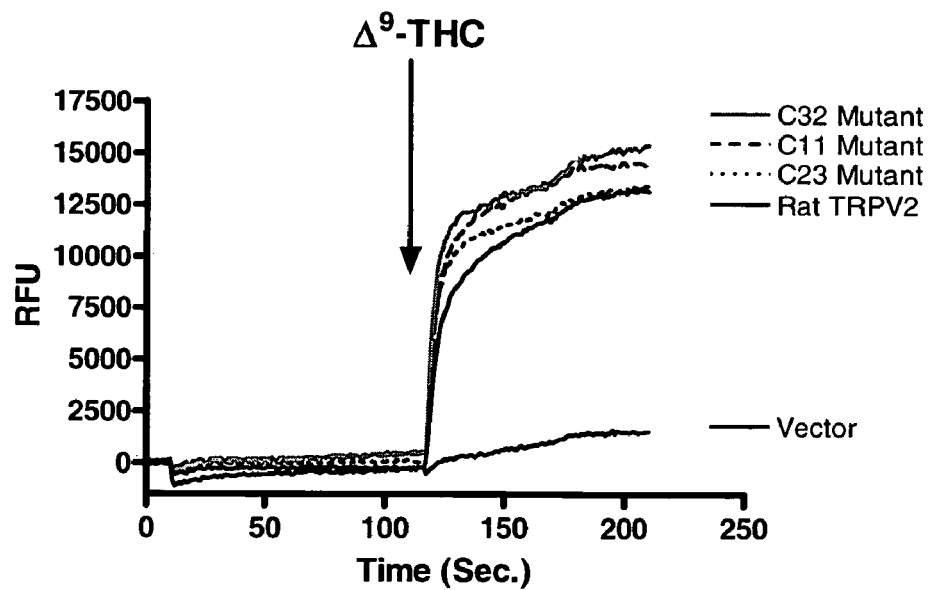

Figure 7
A.
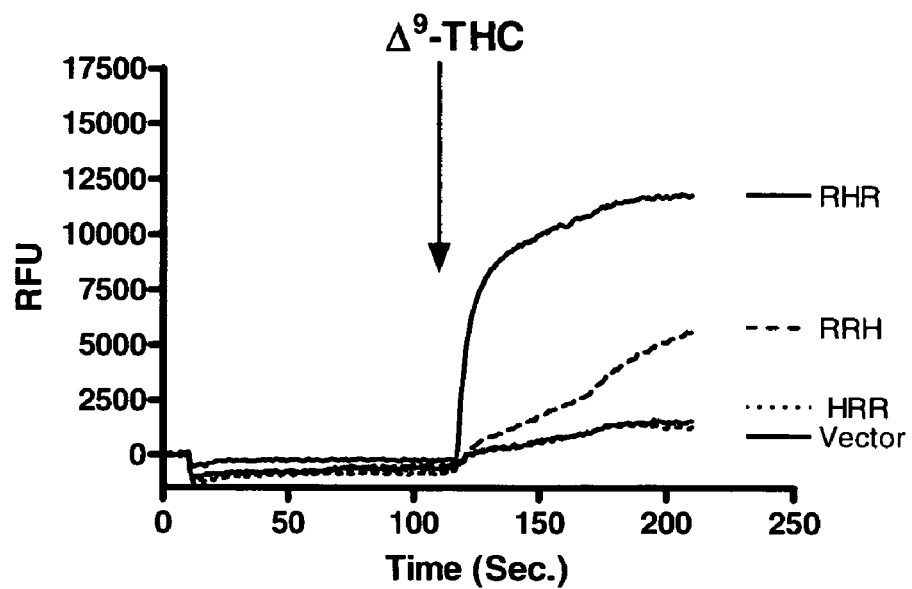
B.
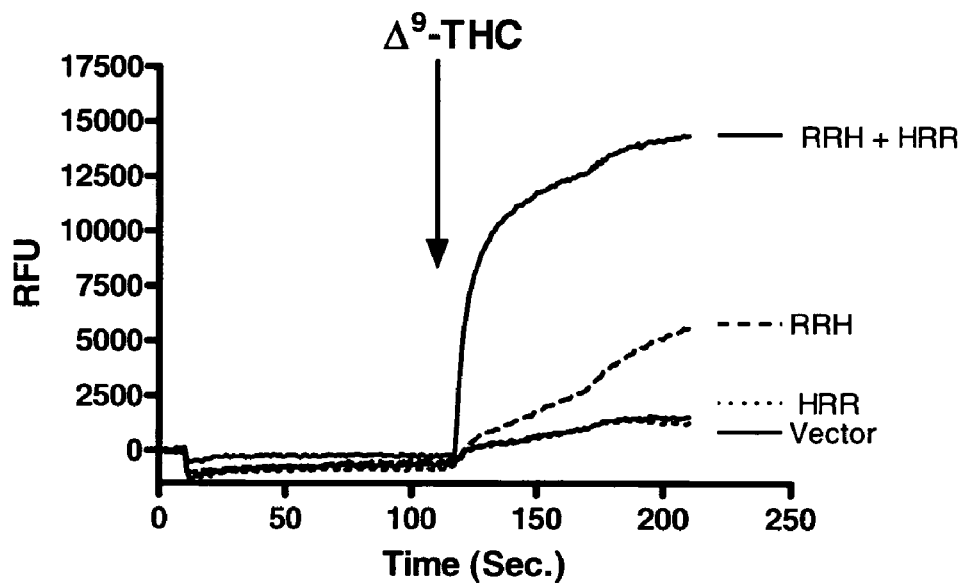

SEQUENCE LISTING

<160> NUMBER OF SEQ ID NOS: 10

<210> SEQ ID NO 1
<211> LENGTH: 2295
<212> TYPE: DNA
<213> ORGANISM: Homo sapiens

<400> SEQUENCE: 1

```
atgacctcac cctccagctc tccagttttc aggttggaga cattagatgg aggccaagaa      60
gatggctctg aggcggacag aggaaagctg gattttggga gcgggctgcc tcccatggag     120
tcacagttcc agggcgagga ccggaaattc gcccctcaga taagagtcaa cctcaactac     180
cgaaagggaa caggtgccag tcagccggat ccaaaccgat ttgaccgaga tcggctcttc     240
aatgcggtct ccggggtgt ccccgaggat ctggctggac ttccagagta cctgagcaag     300
accagcaagt acctcaccga ctcggaatac acagagggct ccacaggtaa gacgtgcctg     360
atgaaggctg tgctgaacct taaggacgga gtcaatgcct gcattctgcc actgctgcag     420
atcgacaggg actctggcaa tcctcagccc ctggtaaatg cccagtgcac agatgactat     480
taccgaggcc acagcgctct gcacatcgcc attgagaaga ggagtctgca gtgtgtgaag     540
ctcctggtgg agaatggggc caatgtgcat gcccgggcct gcggccgctt cttccagaag     600
ggccaaggga cttgctttta tttcggtgag ctacccctct ctttggccgc ttgcaccaag     660
cagtgggatg tggtaagcta cctcctggag aacccacacc agcccgccag cctgcaggcc     720
actgactccc agggcaacac agtcctgcat gccctagtga tgatctcgga caactcagct     780
gagaacattg cactggtgac cagcatgtat gatgggctcc tccaagctgg ggcccgcctc     840
tgccctaccg tgcagcttga ggacatccgc aacctgcagg atctcacgcc tctgaagctg     900
gccgccaagg agggcaagat cgagattttc aggcacatcc tgcagcggga gttttcagga     960
ctgagccacc tttcccgaaa gttcaccgag tggtgctatg ggctgtccg ggtgtcgctg    1020
tatgacctgg cttctgtgga cagctgtgag gagaactcag tgctggagat cattgccttt    1080
cattgcaaga gcccgcaccg acaccgaatg gtcgttttgg agcccctgaa caaactgctg    1140
caggcgaaat gggatctgct catccccaag ttcttcttaa acttcctgtg taatctgatc    1200
tacatgttca tcttcaccgc tgttgcctac catcagccta ccctgaagaa gcaggccgcc    1260
cctcacctga aagcggaggt tggaaactcc atgctgctga cgggccacat ccttatcctg    1320
ctaggggga tctacctcct cgtgggccag ctgtggtact ctggcggcg ccacgtgttc    1380
atctggatct cgttcataga cagctacttt gaaatcctct tcctgttcca ggccctgctc    1440
acagtggtgt cccaggtgct gtgtttcctg gccatcgagt ggtacctgcc cctgcttgtg    1500
tctgcgctgg tgctgggctg gctgaacctg ctttactata cgtggcttt ccagcacaca    1560
ggcatctaca gtgtcatgat ccagaaggtc atcctgcggg acctgctgcg cttccttctg    1620
atctacttag tcttccttttt cggcttcgct gtagccctgt gagcctgag ccaggaggct    1680
tggcgccccg aagctcctac aggccccaat gccacagagt cagtgcagcc catggaggga    1740
caggaggacg agggcaacgg ggcccagtac aggggtatcc tggaagcctc cttggagctc    1800
ttcaaattca ccatcggcat gggcgagctg gccttccagg agcagctgca cttccgcggc    1860
```

```
atggtgctgc tgctgctgct ggcctacgtg ctgctcacct acatcctgct gctcaacatg   1920
ctcatcgccc tcatgagcga gaccgtcaac agtgtcgcca ctgacagctg gagcatctgg   1980
aagctgcaga aagccatctc tgtcctggag atggagaatg gctattggtg gtgcaggaag   2040
aagcagcggg caggtgtgat gctgaccgtt ggcactaagc cagatggcag ccccgatgag   2100
cgctggtgct tcagggtgga ggaggtgaac tgggcttcat gggagcagac gctgcctacg   2160
ctgtgtgagg acccgtcagg ggcaggtgtc cctcgaactc tcgagaaccc tgtcctggct   2220
tcccctccca aggaggatga ggatggtgcc tctgaggaaa actatgtgcc cgtccagctc   2280
ctccagtcca actga                                                    2295
```

<210> SEQ ID NO 2
<211> LENGTH: 764
<212> TYPE: PRT
<213> ORGANISM: Homo sapiens

<400> SEQUENCE: 2

```
Met Thr Ser Pro Ser Ser Pro Val Phe Arg Leu Glu Thr Leu Asp
1               5                   10                  15

Gly Gly Gln Glu Asp Gly Ser Glu Ala Asp Arg Gly Lys Leu Asp Phe
            20                  25                  30

Gly Ser Gly Leu Pro Pro Met Glu Ser Gln Phe Gln Gly Glu Asp Arg
        35                  40                  45

Lys Phe Ala Pro Gln Ile Arg Val Asn Leu Asn Tyr Arg Lys Gly Thr
    50                  55                  60

Gly Ala Ser Gln Pro Asp Pro Asn Arg Phe Asp Arg Asp Arg Leu Phe
65                  70                  75                  80

Asn Ala Val Ser Arg Gly Val Pro Glu Asp Leu Ala Gly Leu Pro Glu
                85                  90                  95

Tyr Leu Ser Lys Thr Ser Lys Tyr Leu Thr Asp Ser Glu Tyr Thr Glu
            100                 105                 110

Gly Ser Thr Gly Lys Thr Cys Leu Met Lys Ala Val Leu Asn Leu Lys
        115                 120                 125

Asp Gly Val Asn Ala Cys Ile Leu Pro Leu Leu Gln Ile Asp Arg Asp
    130                 135                 140

Ser Gly Asn Pro Gln Pro Leu Val Asn Ala Gln Cys Thr Asp Asp Tyr
145                 150                 155                 160

Tyr Arg Gly His Ser Ala Leu His Ile Ala Ile Glu Lys Arg Ser Leu
                165                 170                 175

Gln Cys Val Lys Leu Leu Val Glu Asn Gly Ala Asn Val His Ala Arg
            180                 185                 190

Ala Cys Gly Arg Phe Phe Gln Lys Gly Gln Gly Thr Cys Phe Tyr Phe
        195                 200                 205

Gly Glu Leu Pro Leu Ser Leu Ala Ala Cys Thr Lys Gln Trp Asp Val
    210                 215                 220

Val Ser Tyr Leu Leu Glu Asn Pro His Gln Pro Ala Ser Leu Gln Ala
225                 230                 235                 240

Thr Asp Ser Gln Gly Asn Thr Val Leu His Ala Leu Val Met Ile Ser
                245                 250                 255

Asp Asn Ser Ala Glu Asn Ile Ala Leu Val Thr Ser Met Tyr Asp Gly
            260                 265                 270

Leu Leu Gln Ala Gly Ala Arg Leu Cys Pro Thr Val Gln Leu Glu Asp
        275                 280                 285

Ile Arg Asn Leu Gln Asp Leu Thr Pro Leu Lys Leu Ala Ala Lys Glu
```

```
            290                 295                 300
Gly Lys Ile Glu Ile Phe Arg His Ile Leu Gln Arg Glu Phe Ser Gly
305                 310                 315                 320

Leu Ser His Leu Ser Arg Lys Phe Thr Glu Trp Cys Tyr Gly Pro Val
                325                 330                 335

Arg Val Ser Leu Tyr Asp Leu Ala Ser Val Asp Ser Cys Glu Glu Asn
                340                 345                 350

Ser Val Leu Glu Ile Ile Ala Phe His Cys Lys Ser Pro His Arg His
            355                 360                 365

Arg Met Val Val Leu Glu Pro Leu Asn Lys Leu Gln Ala Lys Trp
370                 375                 380

Asp Leu Leu Ile Pro Lys Phe Phe Leu Asn Phe Leu Cys Asn Leu Ile
385                 390                 395                 400

Tyr Met Phe Ile Phe Thr Ala Val Ala Tyr His Gln Pro Thr Leu Lys
                405                 410                 415

Lys Gln Ala Ala Pro His Leu Lys Ala Glu Val Gly Asn Ser Met Leu
                420                 425                 430

Leu Thr Gly His Ile Leu Ile Leu Leu Gly Gly Ile Tyr Leu Leu Val
            435                 440                 445

Gly Gln Leu Trp Tyr Phe Trp Arg Arg His Val Phe Ile Trp Ile Ser
450                 455                 460

Phe Ile Asp Ser Tyr Phe Glu Ile Leu Phe Leu Phe Gln Ala Leu Leu
465                 470                 475                 480

Thr Val Val Ser Gln Val Leu Cys Phe Leu Ala Ile Glu Trp Tyr Leu
                485                 490                 495

Pro Leu Leu Val Ser Ala Leu Val Leu Gly Trp Leu Asn Leu Leu Tyr
                500                 505                 510

Tyr Thr Arg Gly Phe Gln His Thr Gly Ile Tyr Ser Val Met Ile Gln
            515                 520                 525

Lys Val Ile Leu Arg Asp Leu Leu Arg Phe Leu Leu Ile Tyr Leu Val
530                 535                 540

Phe Leu Phe Gly Phe Ala Val Ala Leu Val Ser Leu Ser Gln Glu Ala
545                 550                 555                 560

Trp Arg Pro Glu Ala Pro Thr Gly Pro Asn Ala Thr Glu Ser Val Gln
                565                 570                 575

Pro Met Glu Gly Gln Glu Asp Glu Gly Asn Gly Ala Gln Tyr Arg Gly
                580                 585                 590

Ile Leu Glu Ala Ser Leu Glu Leu Phe Lys Phe Thr Ile Gly Met Gly
            595                 600                 605

Glu Leu Ala Phe Gln Glu Gln Leu His Phe Arg Gly Met Val Leu Leu
            610                 615                 620

Leu Leu Leu Ala Tyr Val Leu Leu Thr Tyr Ile Leu Leu Leu Asn Met
625                 630                 635                 640

Leu Ile Ala Leu Met Ser Glu Thr Val Asn Ser Val Ala Thr Asp Ser
                645                 650                 655

Trp Ser Ile Trp Lys Leu Gln Lys Ala Ile Ser Val Leu Glu Met Glu
                660                 665                 670

Asn Gly Tyr Trp Trp Cys Arg Lys Lys Gln Arg Ala Gly Val Met Leu
            675                 680                 685

Thr Val Gly Thr Lys Pro Asp Gly Ser Pro Asp Glu Arg Trp Cys Phe
            690                 695                 700

Arg Val Glu Glu Val Asn Trp Ala Ser Trp Gln Thr Leu Pro Thr
705                 710                 715                 720
```

```
Leu Cys Glu Asp Pro Ser Gly Ala Gly Val Pro Arg Thr Leu Glu Asn
            725                 730                 735

Pro Val Leu Ala Ser Pro Pro Lys Glu Asp Glu Asp Gly Ala Ser Glu
        740                 745                 750

Glu Asn Tyr Val Pro Val Gln Leu Leu Gln Ser Asn
        755                 760

<210> SEQ ID NO 3
<211> LENGTH: 2286
<212> TYPE: DNA
<213> ORGANISM: Rattus norvegicus

<400> SEQUENCE: 3
atgacttcag cctccagccc cccagctttc aggctggaga cttccgatgg agatgaagag     60
ggcaatgctg aggtgaacaa ggggaagcag gaaccgcccc ccatggagtc accattccag    120
agggaggacc ggaattcctc ccctcagatc aaagtgaacc tcaacttcat aaagagacct    180
cctaaaaaca cttctgctcc cagccagcag gagccagatc ggtttgaccg tgaccgactc    240
ttcagtgtgg tctcccgggg tgtccccgag gaactgactg gactgctaga ataccttgcgc    300 tggaacagca agtacctcac tgactctgca tacacagaag gctccactgg aaagacgtgc    360
ctgatgaagc tgtgctgaa ccttcaggat ggggtcaatg cctgcatcat gccgctgctg    420
cagattgaca aggattccgg caatcccaag cccctcgtca atgcccagtg catcgatgag    480
ttctaccaag ccacagtgc gctgcacatc gccatagaga gaggagcct gcagtgcgtg    540 aagctgctgg tagagaatgg agcggatgtt cacctccgag cctgtggccg cttcttccaa    600
aagcaccaag gaacttgttt ctattttgga gagctacctc tttctctggc tgcgtgcacc    660
aagcagtggg atgtggtgac ctacctcctg gagaaccccac caccgccggc cagcctggag    720
gccaccgact ccctgggcaa cacagtcctg catgctctgg taatgattgc agataactcg    780
cctgagaaca gtgccctggt gatccacatg tacgacgggc ttctacaaat gggggcgcgc    840
ctctgcccca ctgtgcagct tgaggaaatc tccaaccacc aaggcctcac accctgaaa    900 ctagccgcca aggaaggcaa aatcgagatt ttcaggcaca ttctgcagcg ggaattctca    960
ggaccgtacc agccccttc ccgaaagttt actgagtggt gttacggtcc tgtgcgggta   1020
tcgctgtacg acctgtcctc tgtggacagc tgggaaaaga actcggtgct ggagatcatc   1080
gcttttcatt gcaagagccc gaaccggcac cgcatggtgg ttttagaacc actgaacaag   1140
cttctgcagg agaaatggga tcggctcgtc tcaagattct tcttcaactt cgcctgctac   1200
ttggtctaca tgttcatctt caccgtcgtt gcctaccacc agccttccct ggatcagcca   1260
gccatcccct catcaaaagc gacttttggg gaatccatgc tgctgctggg ccacattctg   1320
atcctgcttg ggggtattta cctcttactg ggccagctgt ggtacttttg gcggcggcgc   1380
ctgttcatct ggatctcatt catggacagc tactttgaaa tcctctttct ccttcaggct   1440
ctgctcacag tgctgtccca ggtgctgcgc ttcatggaga ctgaatggta cctacccctg   1500
ctagtgttat ccctagtgct gggctggctg aacctgcttt actacacacg ggctttcag   1560 cacacaggca tctacagtgt catgatccag aaggtcatcc ttcgagacct gctccgtttc   1620
ctgctggtct acctggtctt ccttttcggc tttgctgtag cctagtaag cttgagcaga   1680 gaggcccgaa gtcccaaagc ccctgaagat aacaactcca cagtgacgga acagcccacg   1740
gtgggccagg aggaggagcc agctccatat cggagcattc tggatgcctc cctagagctg   1800
ttcaagttca ccattggtat gggggagctg gctttccagg aacagctgcg ttttcgtggg   1860
```

```
gtggtcctgc tgttgctgtt ggcctacgtc cttctcacct acgtcctgct gctcaacatg   1920
ctcattgctc tcatgagcga aactgtcaac cacgttgctg acaacagctg gagcatctgg   1980
aagttgcaga aagccatctc tgtcttggag atggagaatg ttactggtg gtgccggagg    2040 aagaaacatc gtgaaggag gctgctgaaa gtcggcacca ggggggatgg taccctgat    2100 gagcgctggt gcttcaggt ggaggaagta aattgggttg cttgggagaa gactcttccc    2160
accttatctg aggatccatc agggccaggc atcactggta ataaaaagaa cccaacctct   2220
aaaccgggga agaacagtgc ctcagaggaa gaccatctgc cccttcaggt cctccagtcc   2280
ccctga                                                              2286
```

<210> SEQ ID NO 4
<211> LENGTH: 761
<212> TYPE: PRT
<213> ORGANISM: Rattus norvegicus

<400> SEQUENCE: 4

```
Met Thr Ser Ala Ser Pro Pro Ala Phe Arg Leu Glu Thr Ser Asp
1               5                   10                  15

Gly Asp Glu Glu Gly Asn Ala Glu Val Asn Lys Gly Lys Gln Glu Pro
            20                  25                  30

Pro Pro Met Glu Ser Pro Phe Gln Arg Glu Asp Arg Asn Ser Ser Pro
        35                  40                  45

Gln Ile Lys Val Asn Leu Asn Phe Ile Lys Arg Pro Pro Lys Asn Thr
    50                  55                  60

Ser Ala Pro Ser Gln Gln Glu Pro Asp Arg Phe Asp Arg Asp Arg Leu
65                  70                  75                  80

Phe Ser Val Val Ser Arg Gly Val Pro Glu Leu Thr Gly Leu Leu
                85                  90                  95

Glu Tyr Leu Arg Trp Asn Ser Lys Tyr Leu Thr Asp Ser Ala Tyr Thr
            100                 105                 110

Glu Gly Ser Thr Gly Lys Thr Cys Leu Met Lys Ala Val Leu Asn Leu
        115                 120                 125

Gln Asp Gly Val Asn Ala Cys Ile Met Pro Leu Leu Gln Ile Asp Lys
    130                 135                 140

Asp Ser Gly Asn Pro Lys Pro Leu Val Asn Ala Gln Cys Ile Asp Glu
145                 150                 155                 160

Phe Tyr Gln Gly His Ser Ala Leu His Ile Ala Ile Glu Lys Arg Ser
                165                 170                 175

Leu Gln Cys Val Lys Leu Leu Val Glu Asn Gly Ala Asp Val His Leu
            180                 185                 190

Arg Ala Cys Gly Arg Phe Phe Gln Lys His Gln Gly Thr Cys Phe Tyr
        195                 200                 205

Phe Gly Glu Leu Pro Leu Ser Leu Ala Ala Cys Thr Lys Gln Trp Asp
    210                 215                 220

Val Val Thr Tyr Leu Leu Glu Asn Pro His Gln Pro Ala Ser Leu Glu
225                 230                 235                 240

Ala Thr Asp Ser Leu Gly Asn Thr Val Leu His Ala Leu Val Met Ile
                245                 250                 255

Ala Asp Asn Ser Pro Glu Asn Ser Ala Leu Val Ile His Met Tyr Asp
            260                 265                 270

Gly Leu Leu Gln Met Gly Ala Arg Leu Cys Pro Thr Val Gln Leu Glu
        275                 280                 285
```

-continued

```
Glu Ile Ser Asn His Gln Gly Leu Thr Pro Leu Lys Leu Ala Ala Lys
290                 295                 300

Glu Gly Lys Ile Glu Ile Phe Arg His Ile Leu Gln Arg Glu Phe Ser
305                 310                 315                 320

Gly Pro Tyr Gln Pro Leu Ser Arg Lys Phe Thr Glu Trp Cys Tyr Gly
                325                 330                 335

Pro Val Arg Val Ser Leu Tyr Asp Leu Ser Ser Val Asp Ser Trp Glu
                340                 345                 350

Lys Asn Ser Val Leu Glu Ile Ile Ala Phe His Cys Lys Ser Pro Asn
            355                 360                 365

Arg His Arg Met Val Val Leu Glu Pro Leu Asn Lys Leu Leu Gln Glu
370                 375                 380

Lys Trp Asp Arg Leu Val Ser Arg Phe Phe Asn Phe Ala Cys Tyr
385                 390                 395                 400

Leu Val Tyr Met Phe Ile Phe Thr Val Ala Tyr His Gln Pro Ser
                405                 410                 415

Leu Asp Gln Pro Ala Ile Pro Ser Ser Lys Ala Thr Phe Gly Glu Ser
                420                 425                 430

Met Leu Leu Gly His Ile Leu Ile Leu Leu Gly Gly Ile Tyr Leu
            435                 440                 445

Leu Leu Gly Gln Leu Trp Tyr Phe Trp Arg Arg Leu Phe Ile Trp
450                 455                 460

Ile Ser Phe Met Asp Ser Tyr Phe Glu Ile Leu Phe Leu Leu Gln Ala
465                 470                 475                 480

Leu Leu Thr Val Leu Ser Gln Val Leu Arg Phe Met Glu Thr Glu Trp
                485                 490                 495

Tyr Leu Pro Leu Leu Val Leu Ser Leu Val Leu Gly Trp Leu Asn Leu
                500                 505                 510

Leu Tyr Tyr Thr Arg Gly Phe Gln His Thr Gly Ile Tyr Ser Val Met
    515                 520                 525

Ile Gln Lys Val Ile Leu Arg Asp Leu Leu Arg Phe Leu Leu Val Tyr
530                 535                 540

Leu Val Phe Leu Phe Gly Phe Ala Val Ala Leu Val Ser Leu Ser Arg
545                 550                 555                 560

Glu Ala Arg Ser Pro Lys Ala Pro Glu Asp Asn Asn Ser Thr Val Thr
                565                 570                 575

Glu Gln Pro Thr Val Gly Gln Glu Glu Pro Ala Pro Tyr Arg Ser
                580                 585                 590

Ile Leu Asp Ala Ser Leu Glu Leu Phe Lys Phe Thr Ile Gly Met Gly
    595                 600                 605

Glu Leu Ala Phe Gln Glu Gln Leu Arg Phe Arg Gly Val Val Leu Leu
610                 615                 620

Leu Leu Leu Ala Tyr Val Leu Leu Thr Tyr Val Leu Leu Asn Met
625                 630                 635                 640

Leu Ile Ala Leu Met Ser Glu Thr Val Asn His Val Ala Asp Asn Ser
                645                 650                 655

Trp Ser Ile Trp Lys Leu Gln Lys Ala Ile Ser Val Leu Glu Met Glu
            660                 665                 670

Asn Gly Tyr Trp Trp Cys Arg Arg Lys Lys His Arg Glu Gly Arg Leu
            675                 680                 685

Leu Lys Val Gly Thr Arg Gly Asp Gly Thr Pro Asp Glu Arg Trp Cys
690                 695                 700

Phe Arg Val Glu Glu Val Asn Trp Val Ala Trp Glu Lys Thr Leu Pro
```

```
                705                 710                 715                 720
Thr Leu Ser Glu Asp Pro Ser Gly Pro Gly Ile Thr Gly Asn Lys Lys
                    725                 730                 735
Asn Pro Thr Ser Lys Pro Gly Lys Asn Ser Ala Ser Glu Glu Asp His
                740                 745                 750
Leu Pro Leu Gln Val Leu Gln Ser Pro
        755                 760

<210> SEQ ID NO 5
<211> LENGTH: 2271
<212> TYPE: DNA
<213> ORGANISM: Mus musculus

<400> SEQUENCE: 5
atgacttcag cctccaaccc cccagctttt aggctggaga cgtccgatgg agatgaagaa      60
ggcagtgctg aggtgaacaa aggaaagaat gagccacccc ccatggagtc tcccttccag     120
ggagaggacc ggaacttctc ccctcagatt aaagtgaatc tcaactaccg aaagggactg     180
ggtcccagcc aacaggaccc aaatcggttt gaccgtgacc gactcttcag tgtggtctcc     240
cggggtgtcc ccgaggagct gactggactg ctagagtacc tgcgccggac cagcaagtac     300
ctcactgact cggcatacac agaaggctcc actggaaaga cgtgcctgat gaaggctgtg     360
ctgaaccttc aggatggggt caatgcctgt atcctgccgc tgctgcagat gacagggat      420 tccggcaatc tcagcccct tgtcaatgcc cagtgcaccg atgagttcta ccgaggccac     480
agtgcgctgc acatcgccat agagaagagg agcctgtggt gcgtgaagct gctggtagag     540
aatggagcga atgttcacat ccgagcctgt ggccgcttct ccaaaagca ccaaggaact     600 tgtttctatt ttggagagct acctctttct ctggcagcgt gcaccaagca gtgggatgtg     660
gtgacctacc tcctggagaa cccacaccag cctgccagcc tggaggccac cgactccctg     720
ggcaacacag tcctgcatgc tctggtaatg attgcagaca actcacctga aacagtgcg      780 ctggtgatcc acatgtatga cagccttctc caaatggggg cccgcctctg ccccactgta     840
cagcttgagg atatctgcaa ccatcaaggc ttaacacccc tgaagttggc tgccaaggaa     900
ggtaaaattg agatcttcag gcacatcctg cagcgggagt tctcagggct gtaccagccc     960 cttttcccgaa agttcaccga tggtgctac ggtcctgtcc gagtgtcact gtacgacctg    1020
tcctctgtgg acagttggga aaagaactcg gtcctggaaa tcatcgcttt ccattgcaag    1080
agcccgcacc ggcaccgcat ggtggtttta gagccactga acaagcttct gcaggagaaa    1140
tgggatcggc tcatcccaag attcttcttc aacttcgcct gttacttggt ctacatgatc    1200
atcttcacca tagttgccta ccaccagcct ccctggagc agccagccat ccctcatca     1260 aaagcgactt tggggactc catgctgctg ttgggccaca ttctgatcct gcttgggggt    1320
atttacctct tactgggcca gctgtggtac ttttggcggc ggcgcctgtt catctggatc    1380
tcgttcatgg acagttactt tgaaatcctc ttccttgtcc aggcgctgct cacagtgctg    1440
tcccaggtgc tgcgcttcgt ggagactgaa tggtacctcc ccctgttagt gtcatcccta    1500
gtgctgggct ggctgaacct gctttattat acacgtggct tcagcacac aggcatctac    1560 agtgtcatga tccaaaaggt cattctgcga gacctgctcc gcttcctgct ggtctaccta    1620
gtcttccttt tcggctttgc tgtagcccta gtaagcttga gccgggaggc ccgaagtccc    1680
aaagcccctg aaaatagcaa caccactgtg acggaaaagc ccacgctggg tcaggaggag    1740
gagccagtcc catatggggg cattctggat gcctccctag agctgttcaa gttcaccatt    1800
```

```
ggtatgggtg agctggcttt ccaggaacag ctgcgctttc gtggggtggt gctgctgttg      1860
ctgttggcct acgtcctcct cacctacgtc ctactgctca acatgctcat tgccctcatg      1920
agtgagactg tcaacagcgt tgccactgac agctggagca tctggaagtt gcagaaagcc      1980
atctctgtct tggagatgga gaatggttac tggtggtgca ggaggaaaag gcatcgcgca      2040 ggaggctgc tgaaagttgg caccaaaggg gatggtatac ctgatgagcg ctggtgcttc       2100
agggtggagg aagtaaactg gctgcatggg agaagaccc ttcccacctt atctgaggat       2160
ccatcagggg caggcatcac tggttataaa aagaacccaa cctctaaacc tgggaagaac      2220
agtgcctcag aggaagacca tctgcctctt caggtcctcc agtcccactg a               2271
```

<210> SEQ ID NO 6
<211> LENGTH: 756
<212> TYPE: PRT
<213> ORGANISM: Mus musculus

<400> SEQUENCE: 6

```
Met Thr Ser Ala Ser Asn Pro Pro Ala Phe Arg Leu Glu Thr Ser Asp
1               5                   10                  15

Gly Asp Glu Glu Gly Ser Ala Glu Val Asn Lys Gly Lys Asn Glu Pro
            20                  25                  30

Pro Pro Met Glu Ser Pro Phe Gln Gly Glu Asp Arg Asn Phe Ser Pro
        35                  40                  45

Gln Ile Lys Val Asn Leu Asn Tyr Arg Lys Gly Leu Gly Pro Ser Gln
    50                  55                  60

Gln Asp Pro Asn Arg Phe Asp Arg Asp Arg Leu Phe Ser Val Val Ser
65                  70                  75                  80

Arg Gly Val Pro Glu Glu Leu Thr Gly Leu Leu Glu Tyr Leu Arg Arg
                85                  90                  95

Thr Ser Lys Tyr Leu Thr Asp Ser Ala Tyr Thr Glu Gly Ser Thr Gly
            100                 105                 110

Lys Thr Cys Leu Met Lys Ala Val Leu Asn Leu Gln Asp Gly Val Asn
        115                 120                 125

Ala Cys Ile Leu Pro Leu Leu Gln Ile Asp Arg Asp Ser Gly Asn Pro
    130                 135                 140

Gln Pro Leu Val Asn Ala Gln Cys Thr Asp Glu Phe Tyr Arg Gly His
145                 150                 155                 160

Ser Ala Leu His Ile Ala Ile Glu Lys Arg Ser Leu Trp Cys Val Lys
                165                 170                 175

Leu Leu Val Glu Asn Gly Ala Asn Val His Ile Arg Ala Cys Gly Arg
            180                 185                 190

Phe Phe Gln Lys His Gln Gly Thr Cys Phe Tyr Phe Gly Glu Leu Pro
        195                 200                 205

Leu Ser Leu Ala Ala Cys Thr Lys Gln Trp Asp Val Val Thr Tyr Leu
    210                 215                 220

Leu Glu Asn Pro His Gln Pro Ala Ser Leu Glu Ala Thr Asp Ser Leu
225                 230                 235                 240

Gly Asn Thr Val Leu His Ala Leu Val Met Ile Ala Asp Asn Ser Pro
                245                 250                 255

Glu Asn Ser Ala Leu Val Ile His Met Tyr Asp Ser Leu Leu Gln Met
            260                 265                 270

Gly Ala Arg Leu Cys Pro Thr Val Gln Leu Glu Asp Ile Cys Asn His
        275                 280                 285

Gln Gly Leu Thr Pro Leu Lys Leu Ala Ala Lys Glu Gly Lys Ile Glu
```

-continued

```
            290                 295                 300
Ile Phe Arg His Ile Leu Gln Arg Glu Phe Ser Gly Leu Tyr Gln Pro
305                 310                 315                 320

Leu Ser Arg Lys Phe Thr Glu Trp Cys Tyr Gly Pro Val Arg Val Ser
                325                 330                 335

Leu Tyr Asp Leu Ser Ser Val Asp Ser Trp Glu Lys Asn Ser Val Leu
                340                 345                 350

Glu Ile Ile Ala Phe His Cys Lys Ser Pro His Arg His Arg Met Val
                355                 360                 365

Val Leu Glu Pro Leu Asn Lys Leu Leu Gln Lys Trp Asp Arg Leu
370                 375                 380

Ile Pro Arg Phe Phe Asn Phe Ala Cys Tyr Leu Val Tyr Met Ile
385                 390                 395                 400

Ile Phe Thr Ile Val Ala Tyr His Gln Pro Ser Leu Glu Gln Pro Ala
                405                 410                 415

Ile Pro Ser Ser Lys Ala Thr Phe Gly Asp Ser Met Leu Leu Gly
                420                 425                 430

His Ile Leu Ile Leu Leu Gly Gly Ile Tyr Leu Leu Leu Gly Gln Leu
                435                 440                 445

Trp Tyr Phe Trp Arg Arg Leu Phe Ile Trp Ile Ser Phe Met Asp
                450                 455                 460

Ser Tyr Phe Glu Ile Leu Phe Leu Val Gln Ala Leu Leu Thr Val Leu
465                 470                 475                 480

Ser Gln Val Leu Arg Phe Val Glu Thr Glu Trp Tyr Leu Pro Leu Leu
                485                 490                 495

Val Ser Ser Leu Val Leu Gly Trp Leu Asn Leu Leu Tyr Tyr Thr Arg
                500                 505                 510

Gly Phe Gln His Thr Gly Ile Tyr Ser Val Met Ile Gln Lys Val Ile
                515                 520                 525

Leu Arg Asp Leu Leu Arg Phe Leu Leu Val Tyr Leu Val Phe Leu Phe
                530                 535                 540

Gly Phe Ala Val Ala Leu Val Ser Leu Ser Arg Glu Ala Arg Ser Pro
545                 550                 555                 560

Lys Ala Pro Glu Asn Ser Asn Thr Thr Val Thr Glu Lys Pro Thr Leu
                565                 570                 575

Gly Gln Glu Glu Glu Pro Val Pro Tyr Gly Gly Ile Leu Asp Ala Ser
                580                 585                 590

Leu Glu Leu Phe Lys Phe Thr Ile Gly Met Gly Glu Leu Ala Phe Gln
                595                 600                 605

Glu Gln Leu Arg Phe Arg Gly Val Val Leu Leu Leu Leu Leu Ala Tyr
                610                 615                 620

Val Leu Leu Thr Tyr Val Leu Leu Asn Met Leu Ile Ala Leu Met
625                 630                 635                 640

Ser Glu Thr Val Asn Ser Val Ala Thr Asp Ser Trp Ser Ile Trp Lys
                645                 650                 655

Leu Gln Lys Ala Ile Ser Val Leu Glu Met Glu Asn Gly Tyr Trp Trp
                660                 665                 670

Cys Arg Arg Lys Arg His Arg Ala Gly Arg Leu Leu Lys Val Gly Thr
                675                 680                 685

Lys Gly Asp Gly Ile Pro Asp Glu Arg Trp Cys Phe Arg Val Glu Glu
                690                 695                 700

Val Asn Trp Ala Ala Trp Glu Lys Thr Leu Pro Thr Leu Ser Glu Asp
705                 710                 715                 720
```

Pro Ser Gly Ala Gly Ile Thr Gly Tyr Lys Lys Asn Pro Thr Ser Lys
            725                 730                 735

Pro Gly Lys Asn Ser Ala Ser Glu Glu Asp His Leu Pro Leu Gln Val
            740                 745                 750

Leu Gln Ser His
        755

<210> SEQ ID NO 7
<211> LENGTH: 706
<212> TYPE: PRT
<213> ORGANISM: Rattus norvegicus

<400> SEQUENCE: 7

Met Thr Ser Ala Ser Ser Pro Ala Phe Arg Leu Glu Thr Ser Asp
1               5                   10                  15

Gly Asp Glu Glu Gly Asn Ala Glu Val Asn Lys Gly Lys Gln Glu Pro
            20                  25                  30

Pro Pro Met Glu Ser Pro Phe Gln Arg Glu Asp Arg Asn Ser Ser Pro
            35                  40                  45

Gln Ile Lys Val Asn Leu Asn Phe Ile Lys Arg Pro Pro Lys Asn Thr
    50                  55                  60

Ser Ala Pro Ser Gln Gln Glu Pro Asp Arg Phe Asp Arg Asp Arg Leu
65                  70                  75                  80

Phe Ser Val Val Ser Arg Gly Val Pro Glu Glu Leu Thr Gly Leu Leu
                85                  90                  95

Glu Tyr Leu Arg Trp Asn Ser Lys Tyr Leu Thr Asp Ser Ala Tyr Thr
            100                 105                 110

Glu Gly Ser Thr Gly Lys Thr Cys Leu Met Lys Ala Val Leu Asn Leu
            115                 120                 125

Gln Asp Gly Val Asn Ala Cys Ile Met Pro Leu Leu Gln Ile Asp Lys
    130                 135                 140

Asp Ser Gly Asn Pro Lys Pro Leu Val Asn Ala Gln Cys Thr Asp Glu
145                 150                 155                 160

Phe Tyr Gln Gly His Ser Ala Leu His Ile Ala Ile Glu Lys Arg Ser
                165                 170                 175

Leu Gln Cys Val Lys Leu Leu Val Glu Asn Gly Ala Asp Val His Leu
            180                 185                 190

Arg Ala Cys Gly Arg Phe Phe Gln Lys His Gln Gly Thr Cys Phe Tyr
            195                 200                 205

Phe Gly Glu Leu Pro Leu Ser Leu Ala Ala Cys Thr Lys Gln Trp Asp
    210                 215                 220

Val Val Thr Tyr Leu Leu Glu Asn Pro His Gln Pro Ala Ser Leu Glu
225                 230                 235                 240

Ala Thr Asp Ser Leu Gly Asn Thr Val Leu His Ala Leu Val Met Ile
                245                 250                 255

Ala Asp Asn Ser Pro Glu Asn Ser Ala Leu Val Ile His Met Tyr Asp
            260                 265                 270

Gly Leu Leu Gln Met Gly Ala Arg Leu Cys Pro Thr Val Gln Leu Glu
            275                 280                 285

Glu Ile Ser Asn His Gln Gly Leu Thr Pro Leu Lys Leu Ala Ala Lys
    290                 295                 300

Glu Gly Lys Ile Glu Ile Phe Arg His Ile Leu Gln Arg Glu Phe Ser
305                 310                 315                 320

Gly Pro Tyr Gln Pro Leu Ser Arg Lys Phe Thr Glu Trp Cys Tyr Gly

```
                    325                 330                 335
Pro Val Arg Val Ser Leu Tyr Asp Leu Ser Ser Val Asp Ser Trp Glu
                340                 345                 350
Lys Asn Ser Val Leu Glu Ile Ile Ala Phe His Cys Lys Ser Pro Asn
            355                 360                 365
Arg His Arg Met Val Leu Glu Pro Leu Asn Lys Leu Leu Gln Glu
        370                 375                 380
Lys Trp Asp Arg Leu Val Ser Arg Phe Phe Asn Phe Ala Cys Tyr
385                 390                 395                 400
Leu Val Tyr Met Phe Ile Phe Thr Val Val Ala Tyr His Gln Pro Ser
                405                 410                 415
Leu Asp Gln Pro Ala Ile Pro Ser Ser Lys Ala Thr Phe Gly Glu Ser
                420                 425                 430
Met Leu Leu Leu Gly His Ile Leu Ile Leu Leu Gly Gly Ile Tyr Leu
                435                 440                 445
Leu Leu Gly Gln Leu Trp Tyr Phe Trp Arg Arg Leu Phe Ile Trp
        450                 455                 460
Ile Ser Phe Met Asp Ser Tyr Phe Glu Ile Leu Phe Leu Leu Gln Ala
465                 470                 475                 480
Leu Leu Thr Val Leu Ser Gln Val Leu Arg Phe Met Glu Thr Glu Trp
                485                 490                 495
Tyr Leu Pro Leu Leu Val Leu Ser Leu Val Leu Gly Trp Leu Asn Leu
                500                 505                 510
Leu Tyr Tyr Thr Arg Gly Phe Gln His Thr Gly Ile Tyr Ser Val Met
            515                 520                 525
Ile Gln Lys Val Ile Leu Arg Asp Leu Leu Arg Phe Leu Leu Val Tyr
        530                 535                 540
Leu Val Phe Leu Phe Gly Phe Ala Val Ala Leu Val Ser Leu Ser Arg
545                 550                 555                 560
Glu Ala Arg Ser Pro Lys Ala Pro Glu Asp Asn Asn Ser Thr Val Thr
                565                 570                 575
Glu Gln Pro Thr Val Gly Gln Glu Glu Glu Pro Ala Pro Tyr Arg Ser
                580                 585                 590
Ile Leu Asp Ala Ser Leu Glu Leu Phe Lys Phe Thr Ile Gly Met Gly
            595                 600                 605
Glu Leu Ala Phe Gln Glu Gln Leu Arg Phe Arg Gly Val Val Leu Leu
        610                 615                 620
Leu Leu Leu Ala Tyr Val Leu Leu Thr Tyr Val Leu Leu Leu Asn Met
625                 630                 635                 640
Leu Ile Ala Leu Met Ser Glu Thr Val Asn His Val Ala Asp Asn Ser
                645                 650                 655
Trp Ser Ile Trp Lys Leu Gln Lys Ala Ile Ser Val Leu Glu Met Glu
                660                 665                 670
Asn Gly Tyr Trp Trp Cys Arg Arg Lys His Arg Glu Gly Arg Leu
            675                 680                 685
Leu Lys Val Gly Thr Arg Gly Asp Gly Thr Pro Asp Glu Arg Trp Cys
        690                 695                 700
Phe Arg
705

<210> SEQ ID NO 8
<211> LENGTH: 729
<212> TYPE: PRT
<213> ORGANISM: Rattus norvegicus
```

<400> SEQUENCE: 8

```
Met Thr Ser Ala Ser Ser Pro Pro Ala Phe Arg Leu Glu Thr Ser Asp
1               5                   10                  15
Gly Asp Glu Glu Gly Asn Ala Glu Val Asn Lys Gly Lys Gln Glu Pro
            20                  25                  30
Pro Pro Met Glu Ser Pro Phe Gln Arg Glu Asp Arg Asn Ser Ser Pro
        35                  40                  45
Gln Ile Lys Val Asn Leu Asn Phe Ile Lys Arg Pro Pro Lys Asn Thr
    50                  55                  60
Ser Ala Pro Ser Gln Gln Glu Pro Asp Arg Phe Asp Arg Asp Arg Leu
65                  70                  75                  80
Phe Ser Val Val Ser Arg Gly Val Pro Glu Glu Leu Thr Gly Leu Leu
                85                  90                  95
Glu Tyr Leu Arg Trp Asn Ser Lys Tyr Leu Thr Asp Ser Ala Tyr Thr
            100                 105                 110
Glu Gly Ser Thr Gly Lys Thr Cys Leu Met Lys Ala Val Leu Asn Leu
        115                 120                 125
Gln Asp Gly Val Asn Ala Cys Ile Met Pro Leu Leu Gln Ile Asp Lys
    130                 135                 140
Asp Ser Gly Asn Pro Lys Pro Leu Val Asn Ala Gln Cys Thr Asp Glu
145                 150                 155                 160
Phe Tyr Gln Gly His Ser Ala Leu His Ile Ala Ile Glu Lys Arg Ser
                165                 170                 175
Leu Gln Cys Val Lys Leu Leu Val Glu Asn Gly Ala Asp Val His Leu
            180                 185                 190
Arg Ala Cys Gly Arg Phe Phe Gln Lys His Gln Gly Thr Cys Phe Tyr
        195                 200                 205
Phe Gly Glu Leu Pro Leu Ser Leu Ala Ala Cys Thr Lys Gln Trp Asp
    210                 215                 220
Val Val Thr Tyr Leu Leu Glu Asn Pro His Gln Pro Ala Ser Leu Glu
225                 230                 235                 240
Ala Thr Asp Ser Leu Gly Asn Thr Val Leu His Ala Leu Val Met Ile
                245                 250                 255
Ala Asp Asn Ser Pro Glu Asn Ser Ala Leu Val Ile His Met Tyr Asp
            260                 265                 270
Gly Leu Leu Gln Met Gly Ala Arg Leu Cys Pro Thr Val Gln Leu Glu
        275                 280                 285
Glu Ile Ser Asn His Gln Gly Leu Thr Pro Leu Lys Leu Ala Ala Lys
    290                 295                 300
Glu Gly Lys Ile Glu Ile Phe Arg His Ile Leu Gln Arg Glu Phe Ser
305                 310                 315                 320
Gly Pro Tyr Gln Pro Leu Ser Arg Lys Phe Thr Glu Trp Cys Tyr Gly
                325                 330                 335
Pro Val Arg Val Ser Leu Tyr Asp Leu Ser Ser Val Asp Ser Trp Glu
            340                 345                 350
Lys Asn Ser Val Leu Glu Ile Ile Ala Phe His Cys Lys Ser Pro Asn
        355                 360                 365
Arg His Arg Met Val Val Leu Glu Pro Leu Asn Lys Leu Leu Gln Glu
    370                 375                 380
Lys Trp Asp Arg Leu Val Ser Arg Phe Phe Asn Phe Ala Cys Tyr
385                 390                 395                 400
Leu Val Tyr Met Phe Ile Phe Thr Val Val Ala Tyr His Gln Pro Ser
```

```
                405                 410                 415
Leu Asp Gln Pro Ala Ile Pro Ser Ser Lys Ala Thr Phe Gly Glu Ser
            420                 425                 430

Met Leu Leu Leu Gly His Ile Leu Ile Leu Leu Gly Gly Ile Tyr Leu
            435                 440                 445

Leu Leu Gly Gln Leu Trp Tyr Phe Trp Arg Arg Leu Phe Ile Trp
            450                 455                 460

Ile Ser Phe Met Asp Ser Tyr Phe Glu Ile Leu Phe Leu Leu Gln Ala
465                 470                 475                 480

Leu Leu Thr Val Leu Ser Gln Val Leu Arg Phe Met Glu Thr Glu Trp
            485                 490                 495

Tyr Leu Pro Leu Leu Val Leu Ser Leu Val Leu Gly Trp Leu Asn Leu
            500                 505                 510

Leu Tyr Tyr Thr Arg Gly Phe Gln His Thr Gly Ile Tyr Ser Val Met
            515                 520                 525

Ile Gln Lys Val Ile Leu Arg Asp Leu Leu Arg Phe Leu Leu Val Tyr
            530                 535                 540

Leu Val Phe Leu Phe Gly Phe Ala Val Ala Leu Val Ser Leu Ser Arg
545                 550                 555                 560

Glu Ala Arg Ser Pro Lys Ala Pro Glu Asp Asn Asn Ser Thr Val Thr
            565                 570                 575

Glu Gln Pro Thr Val Gly Gln Glu Glu Pro Ala Pro Tyr Arg Ser
            580                 585                 590

Ile Leu Asp Ala Ser Leu Glu Leu Phe Lys Phe Thr Ile Gly Met Gly
            595                 600                 605

Glu Leu Ala Phe Gln Glu Gln Leu Arg Phe Arg Gly Val Val Leu Leu
            610                 615                 620

Leu Leu Leu Ala Tyr Val Leu Leu Thr Tyr Val Leu Leu Asn Met
625                 630                 635                 640

Leu Ile Ala Leu Met Ser Glu Thr Val Asn His Val Ala Asp Asn Ser
            645                 650                 655

Trp Ser Ile Trp Lys Leu Gln Lys Ala Ile Ser Val Leu Glu Met Glu
            660                 665                 670

Asn Gly Tyr Trp Trp Cys Arg Arg Lys Lys His Arg Glu Gly Arg Leu
            675                 680                 685

Leu Lys Val Gly Thr Arg Gly Asp Gly Thr Pro Asp Glu Arg Trp Cys
            690                 695                 700

Phe Arg Val Glu Glu Val Asn Trp Ala Ala Trp Glu Lys Thr Leu Pro
705                 710                 715                 720

Thr Leu Ser Glu Asp Pro Ser Gly Pro
            725

<210> SEQ ID NO 9
<211> LENGTH: 738
<212> TYPE: PRT
<213> ORGANISM: Rattus norvegicus

<400> SEQUENCE: 9

Met Thr Ser Ala Ser Ser Pro Pro Ala Phe Arg Leu Glu Thr Ser Asp
1               5                   10                  15

Gly Asp Glu Glu Gly Asn Ala Glu Val Asn Lys Gly Lys Gln Glu Pro
            20                  25                  30

Pro Pro Met Glu Ser Pro Phe Gln Arg Glu Asp Arg Asn Ser Ser Pro
            35                  40                  45
```

```
Gln Ile Lys Val Asn Leu Asn Phe Ile Lys Arg Pro Pro Lys Asn Thr
 50                  55                  60
Ser Ala Pro Ser Gln Gln Glu Pro Asp Arg Phe Asp Arg Asp Arg Leu
 65                      70                  75                  80
Phe Ser Val Val Ser Arg Gly Val Pro Glu Glu Leu Thr Gly Leu Leu
                 85                  90                  95
Glu Tyr Leu Arg Trp Asn Ser Lys Tyr Leu Thr Asp Ser Ala Tyr Thr
            100                 105                 110
Glu Gly Ser Thr Gly Lys Thr Cys Leu Met Lys Ala Val Leu Asn Leu
        115                 120                 125
Gln Asp Gly Val Asn Ala Cys Ile Met Pro Leu Leu Gln Ile Asp Lys
130                 135                 140
Asp Ser Gly Asn Pro Lys Pro Leu Val Asn Ala Gln Cys Thr Asp Glu
145                 150                 155                 160
Phe Tyr Gln Gly His Ser Ala Leu His Ile Ala Ile Glu Lys Arg Ser
                165                 170                 175
Leu Gln Cys Val Lys Leu Leu Val Glu Asn Gly Ala Asp Val His Leu
            180                 185                 190
Arg Ala Cys Gly Arg Phe Phe Gln Lys His Gln Gly Thr Cys Phe Tyr
        195                 200                 205
Phe Gly Glu Leu Pro Leu Ser Leu Ala Ala Cys Thr Lys Gln Trp Asp
210                 215                 220
Val Val Thr Tyr Leu Leu Glu Asn Pro His Gln Pro Ala Ser Leu Glu
225                 230                 235                 240
Ala Thr Asp Ser Leu Gly Asn Thr Val Leu His Ala Leu Val Met Ile
                245                 250                 255
Ala Asp Asn Ser Pro Glu Asn Ser Ala Leu Val Ile His Met Tyr Asp
            260                 265                 270
Gly Leu Leu Gln Met Gly Ala Arg Leu Cys Pro Thr Val Gln Leu Glu
        275                 280                 285
Glu Ile Ser Asn His Gln Gly Leu Thr Pro Leu Lys Leu Ala Ala Lys
290                 295                 300
Glu Gly Lys Ile Glu Ile Phe Arg His Ile Leu Gln Arg Glu Phe Ser
305                 310                 315                 320
Gly Pro Tyr Gln Pro Leu Ser Arg Lys Phe Thr Glu Trp Cys Tyr Gly
                325                 330                 335
Pro Val Arg Val Ser Leu Tyr Asp Leu Ser Ser Val Asp Ser Trp Glu
            340                 345                 350
Lys Asn Ser Val Leu Glu Ile Ile Ala Phe His Cys Lys Ser Pro Asn
        355                 360                 365
Arg His Arg Met Val Val Leu Glu Pro Leu Asn Lys Leu Leu Gln Glu
370                 375                 380
Lys Trp Asp Arg Leu Val Ser Arg Phe Phe Phe Asn Phe Ala Cys Tyr
385                 390                 395                 400
Leu Val Tyr Met Phe Ile Phe Thr Val Val Ala Tyr His Gln Pro Ser
                405                 410                 415
Leu Asp Gln Pro Ala Ile Pro Ser Ser Lys Ala Thr Phe Gly Glu Ser
            420                 425                 430
Met Leu Leu Leu Gly His Ile Leu Ile Leu Leu Gly Gly Ile Tyr Leu
        435                 440                 445
Leu Leu Gly Gln Leu Trp Tyr Phe Trp Arg Arg Arg Leu Phe Ile Trp
450                 455                 460
Ile Ser Phe Met Asp Ser Tyr Phe Glu Ile Leu Phe Leu Leu Gln Ala
```

```
                    465                 470                 475                 480
Leu Leu Thr Val Leu Ser Gln Val Leu Arg Phe Met Glu Thr Glu Trp
                485                 490                 495

Tyr Leu Pro Leu Leu Val Leu Ser Leu Val Leu Gly Trp Leu Asn Leu
            500                 505                 510

Leu Tyr Tyr Thr Arg Gly Phe Gln His Thr Gly Ile Tyr Ser Val Met
            515                 520                 525

Ile Gln Lys Val Ile Leu Arg Asp Leu Leu Arg Phe Leu Leu Val Tyr
        530                 535                 540

Leu Val Phe Leu Phe Gly Phe Ala Val Ala Leu Val Ser Leu Ser Arg
545                 550                 555                 560

Glu Ala Arg Ser Pro Lys Ala Pro Glu Asp Asn Asn Ser Thr Val Thr
                565                 570                 575

Glu Gln Pro Thr Val Gly Gln Glu Glu Pro Ala Pro Tyr Arg Ser
            580                 585                 590

Ile Leu Asp Ala Ser Leu Glu Leu Phe Lys Phe Thr Ile Gly Met Gly
            595                 600                 605

Glu Leu Ala Phe Gln Glu Gln Leu Arg Phe Arg Gly Val Val Leu Leu
        610                 615                 620

Leu Leu Leu Ala Tyr Val Leu Thr Tyr Val Leu Leu Asn Met
625                 630                 635                 640

Leu Ile Ala Leu Met Ser Glu Thr Val Asn His Val Ala Asp Asn Ser
                645                 650                 655

Trp Ser Ile Trp Lys Leu Gln Lys Ala Ile Ser Val Leu Glu Met Glu
            660                 665                 670

Asn Gly Tyr Trp Trp Cys Arg Arg Lys Lys His Arg Glu Gly Arg Leu
            675                 680                 685

Leu Lys Val Gly Thr Arg Gly Asp Gly Thr Pro Asp Glu Arg Trp Cys
        690                 695                 700

Phe Arg Val Glu Glu Val Asn Trp Ala Ala Trp Glu Lys Thr Leu Pro
705                 710                 715                 720

Thr Leu Ser Glu Asp Pro Ser Gly Pro Gly Ile Thr Gly Asn Lys Lys
                725                 730                 735

Asn Pro

<210> SEQ ID NO 10
<211> LENGTH: 750
<212> TYPE: PRT
<213> ORGANISM: Rattus norvegicus

<400> SEQUENCE: 10

Met Thr Ser Ala Ser Ser Pro Pro Ala Phe Arg Leu Glu Thr Ser Asp
1               5                   10                  15

Gly Asp Glu Glu Gly Asn Ala Glu Val Asn Lys Gly Lys Gln Glu Pro
            20                  25                  30

Pro Pro Met Glu Ser Pro Phe Gln Arg Glu Asp Arg Asn Ser Ser Pro
        35                  40                  45

Gln Ile Lys Val Asn Leu Asn Phe Ile Lys Arg Pro Pro Lys Asn Thr
    50                  55                  60

Ser Ala Pro Ser Gln Gln Glu Pro Asp Arg Phe Asp Arg Asp Arg Leu
65                  70                  75                  80

Phe Ser Val Val Ser Arg Gly Val Pro Glu Glu Leu Thr Gly Leu Leu
                85                  90                  95

Glu Tyr Leu Arg Trp Asn Ser Lys Tyr Leu Thr Asp Ser Ala Tyr Thr
```

-continued

```
            100                 105                 110
Glu Gly Ser Thr Gly Lys Thr Cys Leu Met Lys Ala Val Leu Asn Leu
            115                 120                 125
Gln Asp Gly Val Asn Ala Cys Ile Met Pro Leu Leu Gln Ile Asp Lys
            130                 135             140
Asp Ser Gly Asn Pro Lys Pro Leu Val Asn Ala Gln Cys Thr Asp Glu
145                 150                 155                 160
Phe Tyr Gln Gly His Ser Ala Leu His Ile Ala Ile Glu Lys Arg Ser
                165                 170                 175
Leu Gln Cys Val Lys Leu Leu Val Glu Asn Gly Ala Asp Val His Leu
            180                 185                 190
Arg Ala Cys Gly Arg Phe Phe Gln Lys His Gln Gly Thr Cys Phe Tyr
            195                 200                 205
Phe Gly Glu Leu Pro Leu Ser Leu Ala Ala Cys Thr Lys Gln Trp Asp
            210                 215                 220
Val Val Thr Tyr Leu Leu Glu Asn Pro His Gln Pro Ala Ser Leu Glu
225                 230                 235                 240
Ala Thr Asp Ser Leu Gly Asn Thr Val Leu His Ala Leu Val Met Ile
                245                 250                 255
Ala Asp Asn Ser Pro Glu Asn Ser Ala Leu Val Ile His Met Tyr Asp
            260                 265                 270
Gly Leu Leu Gln Met Gly Ala Arg Leu Cys Pro Thr Val Gln Leu Glu
            275                 280                 285
Glu Ile Ser Asn His Gln Gly Leu Thr Pro Leu Lys Leu Ala Ala Lys
            290                 295                 300
Glu Gly Lys Ile Glu Ile Phe Arg His Ile Leu Gln Arg Glu Phe Ser
305                 310                 315                 320
Gly Pro Tyr Gln Pro Leu Ser Arg Lys Phe Thr Glu Trp Cys Tyr Gly
                325                 330                 335
Pro Val Arg Val Ser Leu Tyr Asp Leu Ser Ser Val Asp Ser Trp Glu
            340                 345                 350
Lys Asn Ser Val Leu Glu Ile Ile Ala Phe His Cys Lys Ser Pro Asn
            355                 360                 365
Arg His Arg Met Val Val Leu Glu Pro Leu Asn Lys Leu Leu Gln Glu
            370                 375                 380
Lys Trp Asp Arg Leu Val Ser Arg Phe Phe Phe Asn Phe Ala Cys Tyr
385                 390                 395                 400
Leu Val Tyr Met Phe Ile Phe Thr Val Val Ala Tyr His Gln Pro Ser
                405                 410                 415
Leu Asp Gln Pro Ala Ile Pro Ser Ser Lys Ala Thr Phe Gly Glu Ser
            420                 425                 430
Met Leu Leu Leu Gly His Ile Leu Ile Leu Leu Gly Gly Ile Tyr Leu
            435                 440                 445
Leu Leu Gly Gln Leu Trp Tyr Phe Trp Arg Arg Leu Phe Ile Trp
            450                 455                 460
Ile Ser Phe Met Asp Ser Tyr Phe Glu Ile Leu Phe Leu Leu Gln Ala
465                 470                 475                 480
Leu Leu Thr Val Leu Ser Gln Val Leu Arg Phe Met Glu Thr Glu Trp
                485                 490                 495
Tyr Leu Pro Leu Leu Val Leu Ser Leu Val Leu Gly Trp Leu Asn Leu
            500                 505                 510
Leu Tyr Tyr Thr Arg Gly Phe Gln His Thr Gly Ile Tyr Ser Val Met
            515                 520                 525
```

```
Ile Gln Lys Val Ile Leu Arg Asp Leu Leu Arg Phe Leu Leu Val Tyr
            530                 535                 540

Leu Val Phe Leu Phe Gly Phe Ala Val Ala Leu Val Ser Leu Ser Arg
545                 550                 555                 560

Glu Ala Arg Ser Pro Lys Ala Pro Glu Asp Asn Asn Ser Thr Val Thr
                565                 570                 575

Glu Gln Pro Thr Val Gly Gln Glu Glu Pro Ala Pro Tyr Arg Ser
            580                 585                 590

Ile Leu Asp Ala Ser Leu Glu Leu Phe Lys Phe Thr Ile Gly Met Gly
            595                 600                 605

Glu Leu Ala Phe Gln Glu Gln Leu Arg Phe Arg Gly Val Val Leu Leu
            610                 615                 620

Leu Leu Leu Ala Tyr Val Leu Leu Thr Tyr Val Leu Leu Leu Asn Met
625                 630                 635                 640

Leu Ile Ala Leu Met Ser Glu Thr Val Asn His Val Ala Asp Asn Ser
                645                 650                 655

Trp Ser Ile Trp Lys Leu Gln Lys Ala Ile Ser Val Leu Glu Met Glu
            660                 665                 670

Asn Gly Tyr Trp Trp Cys Arg Arg Lys Lys His Arg Glu Gly Arg Leu
            675                 680                 685

Leu Lys Val Gly Thr Arg Gly Asp Gly Thr Pro Asp Glu Arg Trp Cys
            690                 695                 700

Phe Arg Val Glu Glu Val Asn Trp Ala Ala Trp Glu Lys Thr Leu Pro
705                 710                 715                 720

Thr Leu Ser Glu Asp Pro Ser Gly Pro Gly Ile Thr Gly Asn Lys Lys
                725                 730                 735

Asn Pro Thr Ser Lys Pro Gly Lys Asn Ser Ala Ser Glu Glu
                740                 745                 750
```

COMPOSITIONS AND METHODS FOR IDENTIFYING MODULATORS OF TRPV2

CROSS REFERENCE TO RELATED APPLICATIONS

This application claims priority to Application No. 60/731,686 filed on Oct. 31, 2005 and Application No. 60/782,656 filed on Mar. 15, 2006, the entire contents of which are incorporated by reference herein.

FIELD OF THE INVENTION

The present invention relates to the regulation of thermal receptor ion channel proteins. In particular, the present invention relates to compositions and methods for screening, identifying and characterizing compounds that increase or decrease the biological activity of a TRPV2.

BACKGROUND

In mammals, the sensation of pain triggered by thermal, mechanical or chemical stimuli is a useful warning and protective system. Considerable efforts have been put into elucidating the biochemical mechanisms involved in the detection, transduction and transmission of hot and cold sensations in neuronal tissues. Thermal stimuli activate specialized receptors located on sensory neurons, such as those deriving from the dorsal root ganglion (DRG) and the trigeminal ganglion (TG). When these stimuli are in the noxious range (i.e., very hot or cold), they activate a certain subset of thermal receptors on a sub-population of sensory neurons called nociceptors (pain-sensing neurons). Upon activation, the thermal receptors (e.g., ion channels) transduce the noxious stimulus into an electrical signal that is propagated along the sensory neuron to the spinal cord, where it is relayed to the brain, ultimately leading to the perception of pain. Accordingly, these thermal receptors represent highly promising targets for developing drugs for the treatment of various painful conditions.

Several temperature-activated receptors have been identified with wide ranging temperature sensitivities from noxious heat to noxious cold. These temperature-activated receptors belong to the transient receptor potential (TRP) family of non-selective cation channels, which in *C. elegans* and *D. melanogaster* are involved in mechano- and osmoregulation. Several of these temperature-activated receptors, including TRPV1 and TRPV2, are implicated in noxious heat sensation (Caterina et al., 1997, *Nature,* 389: 816; and Caterina et al., 1999, *Nature* 398: 436). TRPV1, the most extensively characterized member of the thermo-TRP family, is activated by moderate heat (~43° C.), capsaicin, protons and certain endocannabinoids, such as anandamide and 2-AG. It is well accepted that TRPV1 contributes to acute thermal nociception and hyperalgesia after injury (Clapham, *Nature.* 2003, 426(6966): 517-24).

TRPV2, also termed VRL-1, has been proposed as a sensor of noxious temperatures (>52° C.), which presumably mediates "first" pain, i.e. the rapid, acute, and sharp pain evoked by noxious stimuli (Caterina et al., 1999, supra; Story et al., *Cell,* 2003, 112:819-829, and references therein). TRPV2 is structurally most closely related to TRPV1 (~50% sequence identity at the protein level). TRPV2 is expressed in medium- to large- diameter neurons of sensory ganglia, as well as at lower levels in brain, spinal cord, spleen and lung. Furthermore, TRPV2 is upregulated in sympathetic postganglionic neurons following injury, suggesting a potential role for TRPV2 in sympathetically mediated pain (Gaudet et al., *Brain Res.* 2004, 1017(1-2):155-62). Thus, modulation of TRPV2 may potentially have many therapeutic applications.

Despite great interest in TRPV2 modulation, a system for screening, identifying and characterizing TRPV2 modulators has yet to be developed. This is in part due to the lack of known, and in particular, selective TRPV2 agonists, as well as the technical difficulty of assaying these channels in a high temperature environment. In general, TRPV2 does not respond to known TRPV1 agonists (Benham et al., 2003, *Cell Calcium* 33:479-487). However, a recent study reported that 2-aminoethoxydiphenyl borate (2-APB), a non-selective TRP modulator, was able to activate TRPV1, TRPV2, and TRPV3 (Hu et al (2004), *J. Biol. Chem.,* 279: 35741-8), although TRPV2 activation by 2-APB was not observed by others (Chung et al. (2004), *J. Neurosci.* 24: 5177-82).

In an effort to overcome the above-mentioned challenges, the present invention provides novel compositions and methods for screening, identifying and characterizing TRPV2 agonists.

SUMMARY

It has now been discovered that certain cannabinoids specifically activate TRPV2 channel activity.

In one general aspect, the present invention provides a method for identifying a compound that decreases the biological activity of TRPV2, comprising the steps of: a) contacting a TRPV2 polypeptide with a cannabinoid that is capable of activating TRPV2 activity under a condition in which the TRPV2 is activated by the cannabinoid; b) contacting the TRPV2 polypeptide with a test compound; c) measuring the biological activity of the TRPV2 in the presence of both the cannabinoid and the test compound; d) repeating step a); e) measuring the biological activity of the TRPV2 in the presence of the cannabinoid but not the test compound; and f) comparing the TRPV2 activity measured from step c) with that from step e); thereby identifying the compound that decreases the biological activity of TRPV2 when the TRPV2 activity measured from step c) is less than that from step e).

In another general aspect, the present invention provides a method for identifying a compound that increases the biological activity of TRPV2, comprising the steps of: a) obtaining atomic coordinates defining a three-dimensional structure of a complex comprising a TRPV2 interacting with a cannabinoid that is capable of activating the TRPV2; b) elucidating a structural relationship between the TRPV2 and the interacting cannabinoid; c) designing a structural analog of the cannabinoid based on the structural relationship; d) synthesizing the structural analog; and e) determining the extent to which the structural analog alters the biological activity of the TRPV2, thereby identifying the compound that increases the biological activity of TRPV2.

Another general aspect of the present invention is a method for increasing the biological activity of a TRPV2, comprising the step of contacting the TRPV2 with a cannabinoid that is capable of activating the TRPV2 activity.

The present invention further provides a method for stimulating noxious thermo-sensation in a subject, comprising administering to the subject a pharmaceutical composition comprising an effective amount of a cannabinoid that is capable of activating the TRPV2 activity, thereby stimulating the noxious thermo-sensation in the subject.

Other aspects, features and advantages of the invention will be apparent from the following disclosure, including the detailed description of the invention and its preferred embodiments and the appended claims.

DESCRIPTION OF THE FIGURES

FIG. 1 shows the subclasses of cannabinoids present in *Cannabis* (Thakur et al., *Life Sci.* 2005 Oct. 17, Epub ahead of print).

FIG. 3 shows the structures of two representative endocannabinoid (Thakur et al., supra).

FIG. 4 shows concentration-dependent activation of rat TRPV2 by Δ9-THC in a FLIPR assay.

FIG. 5 illustrates activation of both rat and human TRPV2 by Δ9-THC and subsequent block of the Δ9-THC-activated currents by ruthenium red from whole-cell patch clamp studies.

FIG. 6 shows $\Delta^9$-THC activated deletion mutants of TRPV2 recombinantly expressed from HEK293 cells: (A) the N-terminal deletion mutants; and (B) the C-terminal deletion mutants.

FIG. 7 illustrates the activation of the human and rat TRPV2 chimera recombinantly expressed from HEK293 cells: (A) the chimera was expressed individually from the cells; and (B) the complementary effect of RRH and HRR when they were co-expressed from the cells.

DETAILED DESCRIPTION

Figure 2:
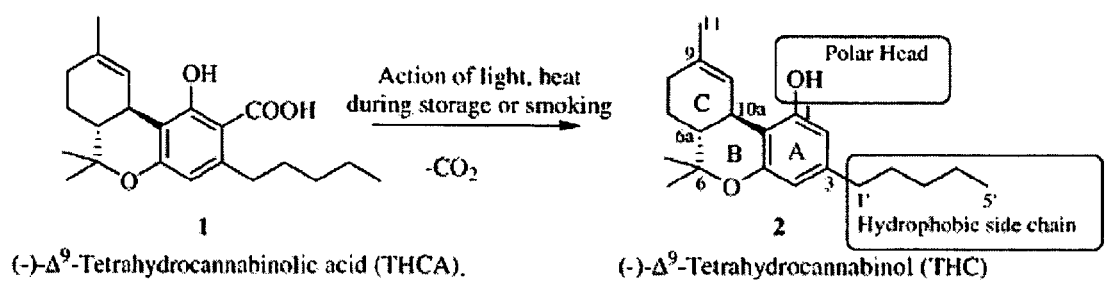
FIG. 2 shows non-enzymatic formation of Δ9-THC from its precursor (Thakur et al., supra).

All publications cited herein are hereby incorporated by reference. Unless defined otherwise, all technical and scientific terms used herein have the same meaning as commonly understood to one of ordinary skill in the art to which this invention pertains.

As used herein, the terms "comprising", "containing", "having" and "including" are used in their open, non-limiting sense.

The following are abbreviations that are at times used in this specification:

2-AG=2-arachidonylglycerol
AEA=anandamide=N-arachidonoylethanolamine
bp=base pair
cDNA=complementary DNA
$Ca^{2+}$=calcium
$\Delta^9$-THC=Delta-9-tetrahydrocannabinol
DRG=dorsal root ganglion
FLIPR=fluorescence imaging plate reader
kb=kilobase; 1000 base pairs
PAGE=polyacrylamide gel electrophoresis
PCR=polymerase chain reaction
SDS=sodium dodecyl sulfate
TG=trigeminal ganglion
TRPV2=transient receptor potential cation channel, subfamily V, member 2

As used herein, the term "biological activity of a TRPV2" refers to an activity exerted by the TRPV2 protein as determined in vivo or in vitro, according to standard techniques. Such an activity can be a direct activity such as the ability of a TRPV2 to bind to a ligand, such as a cannabinoid or an analog thereof. The activity can be the conductivity of an ion channel formed by the TRPV2. The activity can also be functional changes of cell physiology, such as calcium mobilization or nociceptive response of the cell. The biological activity of a TRPV2 can be an indirect activity, such as a signal transduction activity mediated by TRPV2 via its interaction with one or more than one additional protein or other molecule(s).

"Binding affinity" refers to the ability of two or more molecular entities to bind or interact with each other. The binding can be from the formation of one or more chemical bonds that results in continual and stable proximity of the two interacting entities. The binding can also be based solely on physical affinities, which can be equally effective in co-localizing the two interacting entities. Examples of physical affinities and chemical bonds include but are not limited to, forces caused by electrical charge differences, hydrophobicity, hydrogen bonds, van der Waals force, ionic force, covalent linkages, and combinations thereof. The state of proximity between the interacting entities can be transient or permanent, reversible or irreversible. In any event, it is in contrast to and distinguishable from contact caused by natural random movement of two entities.

"Cannabinoid" includes any of various compounds that activate a cannabinoid receptor or a structural analog of the compounds.

In one embodiment, "cannabinoid" includes herbal cannabinoids, a class of compounds that were originally extracted from the plant *Cannabis sativa* L. or a metabolite thereof. *Cannabis sativa* L. is one of the oldest known medicinal plants and has been extensively studied with respect to its phytochemistry. The plant biosynthesizes a total of 483 identified chemical entities belonging to different chemical classes (ElSohly, 2002, In: F. Grotenhermen and E. Russo, Editors, *Cannabis and Cannabinoids*, Haworth Press, Binghamton (2002), pp. 27-36.), of which the cannabinoids are the most distinctive class of compounds, known to exist only in this plant. There are 66 known plant-derived cannabinoids (Thakur et al., *Life Sci.* 2005 Oct. 17, Epub ahead of print). The most prevalent of which are the tetrahydrocannabinols (THCs), the cannabidiols (CBDs), and the cannabinols (CBNs). The next most abundant cannabinoids are the cannabigerols (CBGs), the cannabichromenes (CBCs), and cannabinodiols (CBNDs).

FIG. 1 shows the representative structures of subclasses of cannabinoids present in *Cannabis sativa*. Most cannabinoids contain 21 carbon atoms, but there are some variations in the length of the C-3 side chain attached to the aromatic ring. In the most common homologues, the n-pentyl side chain is replaced with an n-propyl (De Zeeuw et al., *Science.* 1972, 175:778-779); and Vree et al., *Journal of Pharmacy and Pharmacology.* 1972, 24:7-12). These analogues are named using the suffix "varin" and are designated as THCV, CBDV, or CBNV, as examples. Cannabinoids with one (Vree et al., 1972, supra) and four (Smith, 1997, *Journal of Forensic Sciences* 42 (1997), pp. 610-618) carbons also exist but are minor components. Classical cannabinoids (CCs) are ABC tricyclic terpenoid compounds bearing a benzopyran moiety and are insoluble in water but soluble in lipids, alcohols, and other non-polar organic solvents (Thakur et al., 2005, supra). These phenolic derivatives are more water-soluble as their phenolate salts formed under strong alkaline conditions.

One particular example of "cannabinoid" is Delta-9-tetrahydrocannabinol (Delta-9-THC, $\Delta^9$-THC), the key psychoactive ingredient of cannabis (marijuana) (Gaoni and Mechoulam 1964, *Journal of the American Chemical Society* 86 (1964), pp. 1646-1647). As illustrated in FIG. 2, $\Delta^9$-THC is formed by the decarboxylation of its non-psychoactive precursor $\Delta^9$-THCA by the action of light or heat during storage or smoking or under alkaline conditions. $\Delta^9$-THCA is biosynthesized by a well-established pathway involving the action of several specific enzymes.

It was discovered that $\Delta^9$-THC interacts with the two known cannabinoid (CB) receptors, CB1 (Devane et al., 1988, *Molecular Pharmacology* 34 (1988), pp. 605-613; Gerard et al., 1990, *Nucleic Acids Research* 18 (1990), p. 7142; Gerard et al., 1991, *Biochemical Journal* 279 (1991), pp.

129-134; and Matsuda et al., 1990, *Nature* 346 (1990), pp. 561-564.) and CB2 (Munro et al., 1993, *Nature* 365 (1993), pp. 61-65). Both cannabinoid receptors belong to the super family of G-protein coupled receptors, and produce a broad spectrum of physiological effects (Grotenhermen, 2002, In: R. Grotenhermen and E. Russo, Editors, *Cannabis and Cannabinoids*, Haworth Press, Binghamton (2002), pp. 123-142) including antiemetic, appetite enhancing, analgesic, and lowering of intraocular pressure. The discovery of specific cannabinoid receptors inside animal ultimately led to the search and identification of endocannabinoid.

Thus, the term "cannabinoid" also includes endocannabinoid. The term "endocannabinoid" refers to a ligand to a cannabinoid receptor, wherein said ligand is endogenously produced by in the bodies of an animal. Exemplary endocannabinoids include, but are not limited to, N-arachidonoylethanolamine (AEA, anandamide) and 2-arachidonylglycerol (2-AG), the structures of which are shown in FIG. 3. Anandamide was shown to bind to the CB1 receptor with modest affinity ($K_i$=61 nM), have low affinity for the CB2 receptor ($K_i$=1930 nM) (Lin et al., 1998, *Journal of Medicinal Chemistry* 41 (1998), pp. 5353-5361), and behave as a partial agonist in the biochemical and pharmacological tests used to characterize cannabinoid activity. It was reported that anandamide can also bind to and activate TRPV1 (Di Marzo et al., *Prostaglandins Leukot Essent Fatty Acids* 2002; 66: 377-91). 2-AG binds weakly to both CB1 ($K_i$=472 nM) and CB2 ($K_i$=1400 nM) receptors (Mechoulam et al., 1995, *Biochemical Pharmacology* 50 (1995), pp. 83-90). 2-AG was isolated from intestinal and brain tissues and is present in the brain at concentrations approximately 170-fold higher than AEA (3) (Stella et al., 1997, *Nature* 388 (1997), pp. 773-778).

In yet another embodiment, the term "cannabinoid" covers the synthetic cannabinoids are produced by chemical synthesis and do not occur naturally. The synthetic cannabinoids can be synthesized based on the structure of herbal cannabinoids or endocannabinoid. Synthetic cannabinoids are particularly useful in experiments to determine the relationship between the structure and activity of cannabinoid compounds, by making systematic, incremental modifications of cannabinoid molecule. Exemplary synthetic cannabinoids includes dronabinol (synthetic THC), nabilone, and any other synthetic compounds that activate a cannabinoid receptor or a structural analog of the compounds.

A "cannabinoid that is capable of activating the TRPV2 activity" refers to any cannabinoid that is capable of binding to a TRPV2 channel and, in the absence of other stimulation, exhibits at least a 10% increase in the conductivity of the TRPV2 channel compared to the baseline. A person skilled in the art can experimentally determine whether a cannabinoid is capable of activating the TRPV2 activity. In some embodiments, "cannabinoid that is capable of activating the TRPV2 activity" is a cannabinoid which, upon binding to a TRPV2 channel, results in at least a 15%, 20%, 25%, 30%, 35%, 40%, 45%, or 50% increase in the conductivity of the channel compared to the baseline. "Cannabinoid that is capable of activating the TRPV2 activity" includes, but is not limited to, $\Delta^9$-tetrahydrocannabinol, cannabinol, cannabidiol nabilone, CP55940, HU210, and 2-AG. Interestingly, the other endocannabinoid tested, anandamide, showed no or minimal activation effect on TRPV2 (Table 2, Example 4 infra).

A "cannabinoid receptor" or a "CB receptor" each refers to a protein that functions as a specific receptor for a cannabinoid. The "CB receptor" can be a CB1 receptor or a CB2 receptor.

The CB1 receptor has been detected primarily in brain, specifically in the basal ganglia and in the limbic system, including the hippocampus. They are also found in other tissues such as the cerebellum and in both male and female reproductive systems. CB1 receptors appear to be responsible for the euphoric and anticonvulsive effects of *cannabis*. A CB1 can (1) have greater than about 70% amino acid sequence identity to a human CB1 receptor depicted in GenBank protein ID: NP_057167 (the longer isoform of human CB1 receptor) or NP_149421 (the shorter isoform of human CB1 receptor); or (2) bind to antibodies, e.g., polyclonal or monoclonal antibodies, raised against the human CB1 receptor depicted in GenBank protein ID NP_057167 or NP_149421. In some embodiments, the CB1 receptor has greater than about 75, 80, 85, 90, or 95 percent amino acid sequence identity to the human CB1 receptor depicted in GenBank protein ID NP_057167 or NP_149421. The CB1 receptor includes orthologs of the CB1 receptors in animals including human, rat, mouse, pig, dog and monkey, etc. The CB1 receptor also includes structural and functional polymorphisms of the CB1 receptor. "Polymorphism" refers to a set of genetic variants at a particular genetic locus among individuals in a population. The CB1 receptor includes the structural and functional polymorphisms of the CB1 receptor from human (GenBank protein ID NP_057167 or NP_149421), rat (GenBank protein ID: NP_036916), or mouse (GenBank protein ID: NP_031752), or etc.

The CB2 receptor has been detected almost exclusively in the immune system, with the greatest density in the peripheral blood cells. CB2 receptors appear to be responsible for the anti-inflammatory and possible other therapeutic. A CB2 can (1) have greater than about 70% amino acid sequence identity to a human CB2 receptor depicted in GenBank protein ID: NP_001832; or (2) bind to antibodies, e.g., polyclonal or monoclonal antibodies, raised against the human CB2 receptor depicted in GenBank protein ID NP_001832. In some embodiments, the CB2 receptor has greater than about 75, 80, 85, 90, or 95 percent amino acid sequence identity to the human CB2 receptor depicted in GenBank protein ID NP_001832. The CB2 receptor includes orthologs of the CB2 receptors in animals including human, rat, mouse, pig, dog and monkey, etc. The CB2 receptor also includes structural and functional polymorphisms of the CB2 receptor. The CB2 receptor includes the structural and functional polymorphisms of the CB2 receptor from human (GenBank protein ID NP_001832), rat (GenBank protein ID: NP_065418), mouse (GenBank protein ID: NP_034054), or etc.

A "cell" refers to at least one cell or a plurality of cells appropriate for the sensitivity of the detection method. The cell can be present in a cultivated cell culture. The cell can also be present in its natural environment, such as a biological tissue or fluid. Cells suitable for the present invention may be bacterial, but are preferably eukaryotic, and are most preferably mammalian.

A "compound that increases the conductivity of a TRPV2 channel" includes any compound that results in increased passage of ions through the TRPV2 channel. In one embodiment, such a compound is an agonist for the TRPV2 channel that binds to the TRPV2 channel to increase its conductivity. Such a compound triggers, initiates, propagates, or otherwise enhances the channel conductivity. In another embodiment, such a compound is a positive allosteric modulator, which interacts with the TRPV2 channel at allosteric sites different from the agonist-binding site, and potentiates the response of the channel to an agonist.

A "compound that decreases the conductivity of a TRPV2 channel" includes any compound that results in decreased passage of ions through the TRPV2 channel. In one embodiment, such a compound is an antagonist for the TRPV2 channel that binds to the TRPV2 channel to counter, decrease or limit the action of an agonist in either a competitive or non-competitive fashion. In another embodiment, such a compound is a negative allosteric modulator, which interacts with the TRPV2 channel at allosteric sites different from the agonist or antagonist-binding site, and decreases the response of the channel to an agonist. In yet another embodiment, such a compound is an inverse agonist that binds to the TRPV2 channel and decreases the conductivity of the channel in the absence of any other compound, such as an agonist.

"Nucleotide sequence" refers to the arrangement of either deoxyribonucleotide or ribonucleotide residues in a polymer in either single- or double-stranded form. Nucleic acid sequences can be composed of natural nucleotides of the following bases: thymidine, adenine, cytosine, guanine, and uracil; abbreviated T, A, C, G, and U, respectively, and/or synthetic analogs of the natural nucleotides.

An "isolated" nucleic acid molecule is one that is substantially separated from at least one of the other nucleic acid molecules present in the natural source of the nucleic acid, or is substantially free of at least one of the chemical precursors or other chemicals when the nucleic acid molecule is chemically synthesized. An "isolated" nucleic acid molecule can also be, for example, a nucleic acid molecule that is substantially free of at least one of the nucleotide sequences that naturally flank the nucleic acid molecule at its 5' and 3' ends in the genomic DNA of the organism from which the nucleic acid is derived. A nucleic acid molecule is "substantially separated from" or "substantially free of" other nucleic acid molecule(s) or other chemical(s) in preparations of the nucleic acid molecule when there is less than about 30%, 20%, 10%, or 5% (by dry weight) of the other nucleic acid molecule(s) or the other chemical(s) (also referred to herein as a "contaminating nucleic acid molecule" or a "contaminating chemical").

Isolated nucleic acid molecules include, without limitation, separate nucleic acid molecules (e.g., cDNA or genomic DNA fragments produced by PCR or restriction endonuclease treatment) independent of other sequences, as well as nucleic acid molecules that are incorporated into a vector, an autonomously replicating plasmid, a virus (e.g., a retrovirus, adenovirus, or herpes virus), or into the genomic DNA of a prokaryote or eukaryote. In addition, an isolated nucleic acid molecule can include a nucleic acid molecule that is part of a hybrid or fusion nucleic acid molecule. An isolated nucleic acid molecule can be a nucleic acid sequence that is: (i) amplified in vitro by, for example, polymerase chain reaction (PCR); (ii) synthesized by, for example, chemical synthesis; (iii) recombinantly produced by cloning; or (iv) purified, as by cleavage and electrophoretic or chromatographic separation.

The term "oligonucleotide" or "oligo" refers to a single-stranded DNA or RNA sequence of a relatively short length, for example, less than 100 residues long. For many methods, oligonucleotides of about 16-25 nucleotides in length are useful, although longer oligonucleotides of greater than about 25 nucleotides may sometimes be utilized. Some oligonucleotides can be used as "primers" for the synthesis of complimentary nucleic acid strands. For example, DNA primers can hybridize to a complimentary nucleic acid sequence to prime the synthesis of a complimentary DNA strand in reactions using DNA polymerases. Oligonucleotides are also useful for hybridization in several methods of nucleic acid detection, for example, in Northern blotting or in situ hybridization.

The terms "polypeptide," "protein," and "peptide" are used herein interchangeably to refer to amino acid chains in which the amino acid residues are linked by peptide bonds or modified peptide bonds. The amino acid chains can be of any length of greater than two amino acids. Unless otherwise specified, the terms "polypeptide," "protein," and "peptide" also encompass various modified forms thereof. Such modified forms may be naturally occurring modified forms or chemically modified forms. Examples of modified forms include, but are not limited to, glycosylated forms, phosphorylated forms, myristoylated forms, palmitoylated forms, ribosylated forms, acetylated forms, ubiquitinated forms, etc. Modifications also include intra-molecular crosslinking and covalent attachment to various moieties such as lipids, flavin, biotin, polyethylene glycol or derivatives thereof, etc. In addition, modifications may also include cyclization, branching and cross-linking. Further, amino acids other than the conventional twenty amino acids encoded by the codons of genes may also be included in a polypeptide.

An "isolated protein" is one that is substantially separated from at least one of the other proteins present in the natural source of the protein, or is substantially free of at least one of the chemical precursors or other chemicals when the protein is chemically synthesized. A protein is "substantially separated from" or "substantially free of" other protein(s) or other chemical(s) in preparations of the protein when there is less than about 30%, 20%, 10%, or 5% (by dry weight) of the other protein(s) or the other chemical(s) (also referred to herein as a "contaminating protein" or a "contaminating chemical").

Isolated proteins can have several different physical forms. The isolated protein can exist as a full-length nascent or unprocessed polypeptide, or as a partially processed polypeptide or as a combination of processed polypeptides. The full-length nascent polypeptide can be postranslationally modified by specific proteolytic cleavage events that result in the formation of fragments of the full-length nascent polypeptide. A fragment, or physical association of fragments can have the biological activity associated with the full-length polypeptide; however, the degree of biological activity associated with individual fragments can vary.

An isolated polypeptide can be a non-naturally occurring polypeptide. For example, an "isolated polypeptide" can be a "hybrid polypeptide." An "isolated polypeptide" can also be a polypeptide derived from a naturally occurring polypeptide by additions or deletions or substitutions of amino acids. An isolated polypeptide can also be a "purified polypeptide" which is used herein to mean a specified polypeptide in a substantially homogeneous preparation substantially free of other cellular components, other polypeptides, viral materials, or culture medium, or when the polypeptide is chemically synthesized, chemical precursors or by-products associated with the chemical synthesis. A "purified polypeptide" can be obtained from natural or recombinant host cells by standard purification techniques, or by chemical synthesis, as will be apparent to skilled artisans.

"Recombinant" refers to a nucleic acid, a protein encoded by a nucleic acid, a cell, or a viral particle, that has been modified using molecular biology techniques to something other than its natural state. For example, recombinant cells can contain nucleotide sequence that is not found within the native (non-recombinant) form of the cell or can express native genes that are otherwise abnormally, under-expressed, or not expressed at all. Recombinant cells can also contain genes found in the native form of the cell wherein the genes are modified and re-introduced into the cell by artificial means. The term also encompasses cells that contain an endogenous nucleic acid that has been modified without removing the nucleic acid from the cell; such modifications include those obtained, for example, by gene replacement, and site-specific mutation.

A "recombinant host cell" is a cell that has had introduced into it a recombinant DNA sequence. Recombinant DNA sequence can be introduced into host cells using any suitable method including, for example, electroporation, calcium phosphate precipitation, microinjection, transformation, biolistics and viral infection. Recombinant DNA may or may not be integrated (covalently linked) into chromosomal DNA making up the genome of the cell. For example, the recombinant DNA can be maintained on an episomal element, such as a plasmid. Alternatively, with respect to a stably transformed or transfected cell, the recombinant DNA has become integrated into the chromosome so that it is inherited by daughter cells through chromosome replication. This stability is demonstrated by the ability of the stably transformed or transfected cell to establish cell lines or clones comprised of a population of daughter cells containing the exogenous DNA. Recombinant host cells may be prokaryotic or eukaryotic, including bacteria such as *E. coli*, fungal cells such as yeast, mammalian cells such as cell lines of human, bovine, porcine, monkey and rodent origin, and insect cells such as *Drosophila*- and silkworm-derived cell lines. It is further understood that the term "recombinant host cell" refers not only to the particular subject cell, but also to the progeny or potential progeny of such a cell. Because certain modifications can occur in succeeding generations due to either mutation or environmental influences, such progeny may not, in fact, be identical to the parent cell, but are still included within the scope of the term as used herein.

"Sequence identity or similarity", as known in the art, is the relationship between two or more polypeptide sequences or two or more polynucleotide sequences, as determined by comparing the sequences. As used herein, "identity", in the context of the relationship between two or more nucleic acid sequences or two or more polypeptide sequences, refers to the percentage of nucleotide or amino acid residues, respectively, that are the same when the sequences are optimally aligned and analyzed. For purposes of comparing a queried sequence against, for example, the amino acid sequence SEQ ID NO:2, the queried sequence is optimally aligned with SEQ ID NO: 2 and the best local alignment over the entire length of SEQ ID NO:2 is obtained.

Analysis can be carried out manually or using sequence comparison algorithms. For sequence comparison, typically one sequence acts as a reference sequence, to which a queried sequence is compared. When using a sequence comparison algorithm, test and reference sequences are input into a computer, sub-sequence coordinates are designated, if necessary, and sequence algorithm program parameters are designated.

Optimal alignment of sequences for comparison can be conducted, for example, by using the homology alignment algorithm of Needleman & Wunsch, J Mol. Biol., 48:443 (1970). Software for performing Needleman & Wunsch analyses is publicly available through the Institut Pasteur (France) Biological Software website. The NEEDLE program uses the Needleman-Wunsch global alignment algorithm to find the optimum alignment (including gaps) of two sequences when considering their entire length. The identity is calculated along with the percentage of identical matches between the two sequences over the reported aligned region, including any gaps in the length. Similarity scores are also provided wherein the similarity is calculated as the percentage of matches between the two sequences over the reported aligned region, including any gaps in the length. Standard comparisons utilize the EBLOSUM62 matrix for protein sequences and the EDNAFULL matrix for nucleotide sequences. The gap open penalty is the score taken away when a gap is created; the default setting using the gap open penalty is 10.0. For gap extension, a penalty is added to the standard gap penalty for each base or residue in the gap; the default setting is 0.5.

Hybridization can also be used as a test to indicate that two polynucleotides are substantially identical to each other. Polynucleotides that share a high degree of identity will hybridize to each other under stringent hybridization conditions. "Stringent hybridization conditions" has the meaning known in the art, as described in Sambrook et al., *Molecular Cloning: A Laboratory Manual*, Second Edition, Cold Spring Harbor Laboratory, Cold Spring Harbor, N.Y., (1989). An exemplary stringent hybridization condition comprises hybridization in 6× sodium chloride/sodium citrate (SSC) at about 45° C., followed by one or more washes in 0.2×SSC and 0.1% SDS at 50-65° C., depending upon the length over which the hybridizing polynucleotides share complementarity.

A "TRPV2", "transient receptor potential cation channel, subfamily V, member 2", "VRL", "VRL1", "VRL-1", or "vanilloid receptor-like protein 1"each refers to a protein that forms an ion channel, the TRPV2 channel, that can be activated by high temperature and/or low osmolarity, and transduces heat responses in sensory ganglia. The TRPV2 channel can also be activated by certain compounds. An activated TRPV2 channel gates the influx of Ca2+ and other cations (e.g., Na+) through the channel, resulting in membrane depolarization. A TRPV2 protein can (1) have greater than about 70% amino acid sequence identity to a human TRPV2 (hTRPV2) protein depicted in SEQ ID NO: 2 (GenBank protein ID: NP_057197); or (2) bind to antibodies, e.g., polyclonal or monoclonal antibodies, raised against a hTRPV2 protein depicted in SEQ ID NO: 2. In some embodiments, the TRPV2 has greater than about 75, 80, 85, 90, or 95 percent amino acid sequence identity to SEQ ID NO: 2. TRPV2 includes orthologs of the TRPV2 in animals including human, rat, mouse, pig, dog and monkey, etc. TRPV2 also includes structural and functional polymorphisms of the TRPV2 from human, rat (GenBank protein ID: NP_058903, SEQ ID NO:4), mouse (GenBank protein ID: NP_035836, SEQ ID NO:6), or etc. For example, it was found that addition of a hemagglutinin A (HA) epitope tag to the end of the rat TRPV2 C-terminus did not alter the channel properties; and that deletion mutants of rat TRPV2-HA lacking the N-terminal 20, 32, and 65 and C-terminal 11, 23, or 32 amino acid residues of rat TRPV2 were still active in their responses to an elevated temperature of about 53°C., lowered osmolarity, Δ9-THC or 2-APB. Therefore, TRPV2 also includes deletion or modifications of the wild-type TRPV2 that maintains the biological activity of the TRPV2, such as the deletion mutants of rat TRPV2 consisting of the amino acid sequence of SEQ ID NOs: 7-14. Furthermore, TRPV2 also includes chimeras between TRPV2 of different animals. For example, it was found that chimeras (SEQ ID NO: 16) between rat and human TRPV2, named RHR (i.e. Rat 1-392/Human 391-646/Rat 647-761), was also active in its response to an elevation of temperature of about 53°C., Δ9-THC and to 2-APB. In addition, TRPV2 further includes an active ion channel formed by the combination of two or more TRPV2 subunits, which by themselves are inactive or less active. For example, TRPV2 can be an active ion channel formed by the co-expression of the chimera RRH (Rat 1-392/Rat 393-646/Human 647-764; SEQ ID NO: 15) and HRR (Human 1-390/Rat 393-646/Rat 647-761; SEQ ID NO: 17).

"TRPV2 activation temperature" is the temperature at which a TRPV2 channel, in the absence of other stimulation, exhibits at least a 10% increase in its conductivity compared to the baseline. A person skilled in the art can experimentally determine the activation temperature for a TRPV2 channel. In some embodiments, "TRPV2 activation temperature" is the temperature at which a TRPV2 channel exhibits at least a 15%, 20%, 25%, 30%, 35%, 40%, 45%, or 50% increase in its conductivity compared to the baseline. "TRPV2 activation temperature" is typically greater than of about 52° C. In some embodiments, the TRPV2 activation temperature is about 52° C.-55° C. or 55° C.-60° C.

"TRPV2 non-activation temperature" is the temperature that falls outside of the range for a "TRPV2 activation temperature". An exemplary TRPV2 non-activation temperature is room temperature (about 22° C.) or any temperature that is below about 52° C.

"Vector" refers to a nucleic acid molecule into which a heterologous nucleic acid can be or is inserted. Some vectors can be introduced into a host cell allowing for replication of the vector or for expression of a protein that is encoded by the vector or construct. Vectors typically have selectable markers, for example, genes that encode proteins allowing for drug resistance, origins of replication sequences, and multiple cloning sites that allow for insertion of a heterologous sequence. Vectors are typically plasmid-based and are designated by a lower case "p" followed by a combination of letters and/or numbers. Starting plasmids disclosed herein are either commercially available, publicly available on an unrestricted basis, or can be constructed from available plasmids by application of procedures known in the art. Many plasmids and other cloning and expression vectors that can be used in accordance with the present invention are well-known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

"Sequence" means the linear order in which monomers occur in a polymer, for example, the order of amino acids in a polypeptide or the order of nucleotides in a polynucleotide.

In practicing the present invention, many conventional techniques in molecular biology, microbiology and recombinant DNA are used. These techniques are well-known and are explained in, for example, Current Protocols in Molecular Biology, Vols. I, II, and III, F. M. Ausubel, ed. (1997); and Sambrook et al., Molecular Cloning: A Laboratory Manual, Cold Spring Harbor Laboratory Press, Cold Spring Harbor, N.Y. (2001).

It was discovered in the present invention that a group of cannabinoids are capable of activating the TRPV2 but not TRPV1 activity. Thus, the present invention provides new methods for regulating the biological activity of TRPV2 and new methods for identifying compounds that regulate biological activity of TRPV2.

In one embodiment, the TRPV2 used in the present invention is present in a cell. The cell can express TRPV2 endogeneously or recombinantly. One exemplary endogeneous cell for TRPV2 is a dorsal root ganglia (DRG) neuron or trigeminal neurons. Other examples of endogeneous cell for TRPV2 include, but are not limited to, intestine intrinsic neurons, vascular smooth muscle cells, and human hepatoblastoma (HepG2).

It will be apparent to skilled artisans that any recombinant expression methods may be used in the present invention for purposes of expressing the TRPV2. Generally, a nucleic acid encoding TRPV2 can be introduced into a suitable host cell. Exemplary nucleic acid molecules that can be used in the present invention include cDNA that encodes for the full length TRPV2 from human (SEQ ID: 1, GenBank accession No: NM_016113), mouse (SEQ ID NO:5, GenBank accession No: NM_011706), or rat (SEQ ID NO:3 GenBank accession No: NM_017207).

Typically, the nucleic acids, preferably in the form of DNA, are incorporated into a vector to form expression vectors capable of directing the production of the interacting protein member(s) once introduced into a host cell. Many types of vectors can be used for the present invention. Methods for the construction of an expression vector for purposes of this invention should be apparent to skilled artisans apprised of the present disclosure. (See generally, *Current Protocols in Molecular Biology*, Vol. 2, Ed. Ausubel, et al., Greene Publish. Assoc. & Wiley Interscience, Ch. 13, 1988; Glover, *DNA Cloning*, Vol. 11, IRL Press, Wash., D.C., Ch. 3, 1986; Bitter, et al., in *Methods in Enzymology* 153:516-544 (1987); *The Molecular Biology of the Yeast Saccharomyces*, Eds. Strathem et al., Cold Spring Harbor Press, Vols. I and II, 1982; and Sambrook et al., *Molecular Cloning: A Laboratory Manual*, Cold Spring Harbor Press, 1989.)

Generally, the expression vectors include an expression cassette having a promoter operably linked to a DNA encoding an interacting protein member. The promoter can be a native promoter, i.e., the promoter found in naturally occurring cells to be responsible for the expression of the interacting protein member in the cells.

Alternatively, the expression cassette can be a chimeric one, i.e., having a heterologous promoter that is not the native promoter responsible for the expression of the interacting protein member in naturally occurring cells. The expression vector may further include an origin of DNA replication for the replication of the vectors in host cells. Preferably, the expression vectors also include a replication origin for the amplification of the vectors in, e.g., *E. coli*, and selection marker(s) for selecting and maintaining only those host cells harboring the expression vectors.

The thus constructed expression vectors can be introduced into the host cells by any techniques known in the art, e.g., by direct DNA transformation, microinjection, electroporation, viral infection, lipofection, gene gun, and the like. The expression of the protein of interest may be transient or stable. The expression vectors can be maintained in host cells in an extrachromosomal state, i.e., as self-replicating plasmids or viruses. Alternatively, the expression vectors can be integrated into chromosomes of the host cells by conventional techniques such as selection of stable cell lines or site-specific recombination. In stable cell lines, at least the expression cassette portion of the expression vector is integrated into a chromosome of the host cells.

The vector construct can be designed to be suitable for expression in various host cells, including but not limited to bacteria, yeast cells, plant cells, insect cells, and mammalian and human cells. Methods for preparing expression vectors for expression in different host cells should be apparent to a skilled artisan. As described in the Example 1, infra, rat and human TRPV2 has been successfully expressed in HEK293.

Homologues and fragments of TRPV2 can also be easily expressed using the recombinant methods described above. For example, to express a protein fragment, the DNA fragment incorporated into the expression vector can be selected such that it only encodes the protein fragment. Likewise, a specific hybrid protein can be expressed using a recombinant DNA encoding the hybrid protein. Similarly, a homologue protein may be expressed from a DNA sequence encoding the homologue protein. A homologue-encoding DNA sequence may be obtained by manipulating the native protein-encoding sequence using recombinant DNA techniques. For this purpose, random or site-directed mutagenesis can be conducted using techniques generally known in the art. To make protein derivatives, for example, the amino acid sequence of a native interacting protein member may be changed in predetermined manners by site-directed DNA mutagenesis to create or remove consensus sequences.

In other embodiments, the TRPV2 is provided in a cell membrane. The membrane preparation can be isolated from a native host cell, for example, a DRG or TG cell, which expresses TRPV2 on its cell surface. The membrane preparation can also be isolated from a recombinant host cell, for example, a CHO, HEK293, or COS cell, which expresses a TRPV2 recombinantly on its cell surface. The membrane preparation can be further prepared from the biological membranes, such as the tissue membrane, plasma membrane, cell membrane, or internal organelle membrane expressing the TRPV2 channels. Methods are known to those skilled in the art for isolation and preparation of biological membrane preparations. For example, such a method can include the steps of mechanical or enzymatic disruption of the tissue or cells, centrifugation to separate the membranes from other components, and resuspending the membrane fragments or vesicles in suitable buffer solution. Alternatively, the membrane-containing preparation can also be derived from artificial membranes. Purified TRPV2 protein can be reconstituted into lipid bilayers to form artificial membrane vesicles (see Chen et al., 1996, *J. Gen. Physiol.* 108:237-250). Such type of membrane vesicle can be very specific to the channel of interest, avoiding the problem of contamination from other channels. For example, such artificial membranes can include an electrode to which is tethered a lipid membrane containing ion channels and forming ion reservoirs. Methods are known to those skilled in the art to prepare artificial membrane vesicles.

In some preferred embodiments, membranes can be broken under controlled conditions, yielding portions of cell membranes and/or membrane vesicles. Cell membrane portions and/or vesicles can, in some embodiments, provide an easier format for the inventive assays and methods, since cell lysis and/or shear is not as much of a concern during the assay. Cell membranes can be derived from tissues and/or cultured cells. Such methods of breaking cell membranes and stabilizing them are known in the art. Methods of treating tissues to obtain cell membranes are known in the art.

Preferably, human TRPV2 is used in the assays of the invention. Optionally, TRPV2 orthologs from other species such as rat or mouse, preferably a mammalian species, are used in assays of the invention.

The compound identification methods can be performed using conventional laboratory formats or in assays adapted for high throughput. The term "high throughput" refers to an assay design that allows easy screening of multiple samples simultaneously and/or in rapid succession, and can include the capacity for robotic manipulation. Another desired feature of high throughput assays is an assay design that is optimized to reduce reagent usage, or minimize the number of manipulations in order to achieve the analysis desired. Examples of assay formats include 96-well or 384-well plates, levitating droplets, and "lab on a chip" microchannel chips used for liquid handling experiments. It is well known by those in the art that as miniaturization of plastic molds and liquid handling devices are advanced, or as improved assay devices are designed, greater numbers of samples can be processed using the design of the present invention.

Any test compounds may be screened in the screening assays of the present invention to select modulators of the protein complex of the invention. By the term "selecting" or "select" compounds it is intended to encompass both (a) choosing compounds from a group previously unknown to be modulators of a protein complex or interacting protein members thereof; and (b) testing compounds that are known to be capable of binding, or modulating the functions and activities of, a protein complex or interacting protein members thereof. Both types of compounds are generally referred to herein as "test compounds" or "candidate compound". The candidate compounds encompass numerous chemical classes, including but not limited to, small organic or inorganic compounds, natural or synthetic molecules, such as antibodies, proteins or fragments thereof, antisense nucleotides, interfering RNA (iRNA) and ribozymes, and derivatives, mimetics and analogs thereof. Preferably, they are small organic compounds, i.e., those having a molecular weight of no greater than 10,000 daltons, more preferably less than 5,000 daltons. Preferably, the test compounds are provided in library formats known in the art, e.g., in chemically synthesized libraries (See generally, Gordan et al. *J. Med. Chem.*, 37:1385-1401 (1994)), recombinantly expressed libraries (e.g., phage display libraries), and in vitro translation-based libraries (e.g., ribosome display libraries).

Candidate compounds comprise functional chemical groups necessary for structural interactions with polypeptides, and typically include at least an amine, carbonyl, hydroxyl or carboxyl group, preferably at least two of the functional chemical groups and more preferably at least three of the functional chemical groups. The candidate compounds can comprise cyclic carbon or heterocyclic structure and/or aromatic or polyaromatic structures substituted with one or more of the above-identified functional groups. Candidate compounds also can be biomolecules such as peptides, saccharides, fatty acids, sterols, isoprenoids, purines, pyrimidines, derivatives or structural analogs of the above, or combinations thereof and the like. Where the compound is a nucleic acid, the compound typically is a DNA or RNA molecule, although modified nucleic acids having non-natural bonds or subunits are also contemplated.

Candidate compounds are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Candidate compounds can also be obtained using any of the numerous approaches in combinatorial library methods known in the art, including biological libraries; spatially addressable parallel solid phase or solution phase libraries: synthetic library methods requiring deconvolution; the "one-bead one-compound" library method; and synthetic library methods using affinity chromatography selection (Lam (1997) *Anticancer Drug Des.* 12:145). Alternatively, libraries of natural compounds in the form of bacterial, fungal, plant and animal extracts are available or readily produced. Additionally, natural and synthetically produced libraries and compounds can be readily modified through conventional chemical, physical, and biochemical means.

Further, known pharmacological agents can be subjected to directed or random chemical modifications such as acylation, alkylation, esterification, amidation, etc. to produce structural analogs of the agents. Candidate compounds can be selected randomly or can be based on existing compounds that bind to and/or modulate the function of TRPV2 activity. Therefore, a source of candidate agents is one or more than one library of molecules based on one or more than one known compound that increases or decreases TRPV2 channel conductivity in which the structure of the compound is changed at one or more positions of the molecule to contain more or fewer chemical moieties or different chemical moieties. The structural changes made to the molecules in creating the libraries of analog activators/inhibitors can be directed, random, or a combination of both directed and random substitutions and/or additions. One of ordinary skill in the art in the preparation of combinatorial libraries can readily prepare such libraries based on the existing compounds.

A variety of other reagents also can be included in the mixture. These include reagents such as salts, buffers, neutral proteins (e.g., albumin), detergents, etc. that can be used to facilitate optimal protein-protein and/or protein-nucleic acid binding. Such a reagent can also reduce non-specific or background interactions of the reaction components. Other reagents that improve the efficiency of the assay such as nuclease inhibitors, antimicrobial agents, and the like can also be used.

Examples of methods for the synthesis of molecular libraries can be found in the art, for example in: Zuckermann et al. (1994). *J. Med. Chem.* 37:2678. Libraries of compounds can be presented in solution (e.g., Houghten (1992) *Biotechniques* 13:412-421), or on beads (Lam (1991) *Nature* 354:82-84), chips (Fodor (1993) *Nature* 364:555-556), bacteria (U.S. Pat. No. 5,223,409), spores (U.S. Pat. No. 5,571,698), plasmids (Cull et al. (1992) *Proc. Natl. Acad. Sci. USA* 89:1865-1869) or phage (see e.g., Scott and Smith (1990) *Science* 249:3 86-390).

The selected compounds can be tested for their ability to decrease the channel conductivity of the TRPV2, or for their ability to decrease the binding activity of the TRPV2 to a cannabinoid that is capable of activating the TRPV2. During the test, the test compound can be added to the TRPV2 prior to, after, or simultaneously with cannabinoid that is capable of activating the TRPV2. In addition, the compounds can be tested in an animal model for pain, or inflammation, etc.

Generally, a control assay is performed in which the above screening assay is conducted in the absence of the test compound. The result of this assay is then compared with that obtained in the presence of the test compound.

The test compounds may be screened in an in vitro assay to identify compounds capable of binding to a TRPV2. For this purpose, a test compound is contacted with TRPV2 under conditions and for a time sufficient to allow specific interaction between the test compound and the TRPV2 to occur, thereby resulting in the binding of the compound to the TRPV2, and the formation of a complex. Subsequently, the binding event is detected.

In one particular embodiment, the TRPV2 is immobilized on a solid support (such as a protein microchip) or on a cell surface or a membrane. For example, the protein complex can be immobilized directly onto a microchip substrate such as glass slides or onto multi-well plates using non-neutralizing antibodies, i.e., antibodies capable of binding to the complex but do not substantially affect its biological activities. A cannabinoid labeled with a detectable marker is contacted with the immobilized TRPV2. Test compounds can be contacted with the immobilized TRPV2 protein to allow binding to occur under standard binding assay conditions. To identify compound binding to aTRPV2, one can measure the detectable marker associated with TRPV2 or disassociated from the TRPV2. A test compound that binds competitively with the labeled cannabinoid to the TRPV2 will result in less binding of TRPV2 to the cannabinoid, thus less labeling associated with TRPV2.

In one embodiment, the test compound can be further evaluated for its ability to increase or decrease the ion conductivity of a TRPV2 channel. Known to those skilled in the art are methods for measuring a TRPV2 channel conductivity, for example, via the cellular depolarization/hyperpolarization or an increase in intracellular calcium ion levels. The level of intracellular calcium can be assessed using a calcium ion-sensitive fluorescent indicator, such as a calcium ion-sensitive fluorescent dye. Suitable calcium ion-sensitive fluorescent dyes include, for example, quin-2 (see, e.g., Tsien et al., J. Cell Biol., 94:325, 1982), fura-2 (see, e.g., Grynkiewicz et al., J. Biol. Chem., 260:3440, 1985), fluo-3 (see, e.g., Kao et al., J. Biol.-43 Chem., 264:8179, 1989) and rhod-2 (see, e.g., Tsien et al., J. Biol. Chem., Abstract 89a, 1987). Suitable calcium ion-sensitive fluorescent dyes are commercially available from, for example, Invitrogen (Molecular Probes Products, Eugene, Oreg.). Cellular fluorescence can also be monitored using a fluorometer or a flow cytometer having a fluorescence lamp and detector. FLIPR assay has been used routinely in measuring the ion conductivity.

The TRPV2 cation channels function to transport not only divalent cations, for example, $Ca^{2+}$, but also monovalent cations, for example, $Na^+$ or $K^+$. Therefore, assays for determining changes in the transport of monovalent cation can also be performed to measure the conductivity of a TRPV2 channel. $Na^+$- and $K^+$-sensitive dyes are known in the art and commercially available from, for example, Invitrogen (Molecular Probes Products, Eugene, Oreg.).

The conductivity of a TRPV2 channel can also be measured by electrophysiologic techniques such as patch clamp. Patch clamp techniques are routinely used for studying electrical activities in cells, cell membranes, and isolated tissues. It involves forming an electrically tight, high-resistance seal between a micropipette and the plasma membrane. The current flowing through individual ion channels within the plasma membrane can then be measured. Different variants on the techniques allow different surfaces of the plasma membrane to be exposed to the bathing medium. The four most common variants include cell-attached, inside-out, outside-out and whole-cell patch clamp.

A patch-clamp method is commonly used with a voltage clamp that controls the voltage across the membrane and measures current flow. For example, in the case of whole-cell patch clamp, during the voltage clamp process, a microelectrode is inserted into a cell and current injected through the electrode so as to hold the cell membrane potential at some predefined level. A patch-clamp method can also be used in the current-clamp configuration, in which the current is controlled and the membrane potential is measured.

In another embodiment, the test compound can be further evaluated by administering it to a live animal. This can be useful to establish efficacy, toxicity and other pharmacological parameters important for establishing dosing regimens. For example, the compound can be administered to a dog to examine various pharmacological aspects of the compound in the dog. The dog testing can be particularly advantageous for identifying and establishing dosing regimens in humans, because dogs, particularly large breeds, are closer in weight to humans as compared to rats or mice and therefore provide a more suitable animal model for estimating human dosing.

The compound can also be administered to animals to assess the ability of the compound to alter nociceptive processes. Various animal models of pain exist. For example, the rat spinal nerve ligation (SNL) model of nerve injuries a model of neuropathic pain (Kim and Chung, Pain, 50:355-363, 1992).

Other suitable animal models of pain can be utilized in connection with the teachings herein. Commonly studied rodent models of neuropathic pain include the chronic constriction injury (CCI) or the Bennett model; neuroma or axotomy model; and the partial sciatic transection or Seltzer model (Shir et al., *Neurosci. Lett.,* 115:62-67, 1990). Exemplary neuropathic pain models include several traumatic nerve injury preparations (Bennett et al., *Pain* 33: 87-107, 1988; Decosterd et al., *Pain* 87: 149-58, 2000; Kim et al., *Pain* 50: 355-363, 1992; Shir et al., *Neurosci Lett* 115: 62-7, 1990), neuroinflammation models (Chacur et al., *Pain* 94: 231-44, 2001; Milligan et al., *Brain Res* 861: 105-16, 2000), diabetic neuropathy (Calcutt et al., *Br J Pharmacol* 122: 1478-82, 1997), virus-induced neuropathy (Fleetwood-Walker et al., *J Gen Virol* 80: 2433-6, 1999), vincristine neuropathy (Aley et al., *Neuroscience* 73: 259-65, 1996; Nozaki-Taguchi et al., *Pain* 93: 69-76, 2001), and paclitaxel neuropathy (Cavaletti et al., *Exp Neurol* 133: 64-72, 1995), as well as acute nociceptive models and inflammatory models (Brennan, T. J. et al. *Pain* 64:493, 1996; D'Amour, F. E. and Smith, D. L. *J Pharmacol* 72: 74-79, 1941; Eddy, N. B. et al. *J Pharmacol Exp Ther* 98:121, 1950; Haffner, F. *Dtsch Med Wochenschr* 55:731, 1929; Hargreaves, K. et al. *Pain* 32: 77-88, 1988; Hunskaar, S. et al. *J Neurosci Meth* 14:69, 1985; Randall, L. O. and Selitto, J. J. *Arch. Int. Pharmacodyn* 111: 409-419, 1957; Siegmund, E. et al. *Proc Soc Exp Bio Med* 95:729, 1957).

The discovery that certain cannabinoids activate TRPV2 also provides new methods for identifying additional compounds that increase the biological activity of TRPV2. Such methods can be based on rational drug design. Structural analogs or mimetics of the cannabinoid can be produced based on rational drug design with the aim of improving drug potency, efficacy and stability, and reducing side effects. Methods known in the art for rational drug design can be used in the present invention. See, e.g., Hodgson et al., *Bio/Technology,* 9:19-21 (1991); U.S. Pat. Nos. 5,800,998 and 5,891,628, all of which are incorporated herein by reference.

Molecular modeling programs can be used to determine whether a small molecule can fit into a functionally relevant portion, for example, an active site, of the TRPV2 polypeptide. Basic information on molecular modeling is provided in, for example, M. Schlecht, Molecular Modeling on the PC, 1998, John Wiley & Sons; Gans et al., Fundamental Principals of Molecular Modeling, 1996, Plenum Pub. Corp.; N.C. Cohen (editor), Guidebook on Molecular Modeling in Drug Design, 1996, Academic Press; and W. B. Smith, Introduction to Theoretical Organic Chemistry and Molecular Modeling, 1996. U.S. Patents that provide detailed information on molecular modeling include U.S. Pat. Nos. 6,093,573; 6,080,576; 5,612,894; and 5,583,973.

Programs that can be useful for molecular modeling studies include, for example, GRID (Goodford, P. J., "A Computational Procedure for Determining Energetically Favorable Binding Sites on Biologically Important Macromolecules" J. Med. Chem., 28, pp. 849-857, 1985), available from Oxford University, Oxford, UK; MCSS (Miranker, A. and M. Karplus, "Functionality Maps of Binding Sites: A Multiple Copy Simultaneous Search Method." Proteins: Structure, Function and Genetics, 11, pp. 29-34, 1991), available from Molecular Simulations, Burlington, Mass.; AUTODOCK (Goodsell, D. S. and A. J. Olsen, "Automated Docking of Substrates to Proteins by Simulated Annealing" Proteins: Structure. Function, and Genetics, 8, pp. 195-202, 1990); available from Scripps Research Institute, La Jolla, Calif.; and DOCK (Kuntz, I. D. et al., "A Geometric Approach to Macromolecule-Ligand Interactions" J. Mol. Biol., 161, pp. 269-288, 1982), available from University of California, San Francisco, Calif.

In this respect, structural information on the TRPV2-cannabinoid complex is obtained. Preferably, atomic coordinates defining a three-dimensional structure of the complex can be obtained. For example, the interacting TRPV2-cannabinoid complex can be studied using various biophysical techniques including, e.g., X-ray crystallography, NMR, computer modeling, mass spectrometry, and the like. Likewise, structural information can also be obtained from protein complexes formed by interacting proteins and a compound that initiates or stabilizes the interaction of the proteins. Methods for obtaining such atomic coordinates by X-ray crystallography, NMR, and the like are known in the art and the application thereof to the target protein or protein complex of the present invention should be apparent to skilled persons in the art of structural biology. See Smyth and Martin, *Mol. Pathol.,* 53:8-14 (2000); Oakley and Wilce, *Clin. Exp. Pharmacol. Physiol.,* 27(3):145-151 (2000); Ferentz and Wagner, Q. *Rev. Biophys.,* 33:29-65 (2000); Hicks, *Curr. Med. Chem.,* 8(6):627-650 (2001); and Roberts, *Curr. Opin. Biotechnol.,* 10:42-47 (1999).

The domains, residues or moieties of a cannabinoid critical to TRPV2-cannabinoid interaction constitute the active region of the cannabinoid known as its "pharmacophore." Once the pharmacophore has been elucidated, a structural model can be established by a modeling process that may incorporate data from NMR analysis, X-ray diffraction data, alanine scanning, spectroscopic techniques and the like. Various techniques including computational analysis (e.g., molecular modeling and simulated annealing), similarity mapping and the like can all be used in this modeling process. See e.g., Perry et al., in *OSAR: Quantitative Structure-Activity Relationships in Drug Design,* pp. 189-193, Alan R. Liss, Inc., 1989; Rotivinen et al., *Acta Pharmaceutical Fennica,* 97:159-166 (1988); Lewis et al., *Proc. R. Soc. Lond.,* 236: 125-140 (1989); McKinaly et al., *Annu. Rev. Pharmacol. Toxiciol.,* 29:111-122 (1989). Commercially available molecular modeling systems from Polygen Corporation, Waltham, Mass., include the CHARMm program, which performs energy minimization and molecular dynamics functions, and QUANTA program, which performs construction, graphic modeling and analysis of molecular structure. Such programs allow interactive construction, modification, and visualization of molecules. Other computer modeling programs are also available from BioDesign, Inc. (Pasadena, Calif.), Hypercube, Inc. (Cambridge, Ontario), and Allelix, Inc. (Mississauga, Ontario, Canada).

A template can be formed based on the established model. Various compounds can then be designed by linking various chemical groups or moieties to the template. Various moieties of the template can also be replaced. In addition, in the case of a peptide lead compound, the peptide or mimetics thereof can be cyclized, e.g., by linking the N-terminus and C-terminus together, to increase its stability. These rationally designed compounds are further tested. In this manner, pharmacologically acceptable and stable compounds with improved potency/efficacy and reduced side effects can be developed. The compounds identified in accordance with the present invention can be incorporated into a pharmaceutical formulation suitable for administration to an individual.

In addition, the structural models or atomic coordinates defining a three-dimensional structure of the target protein or protein complex can also be used in virtual screen to select compounds capable of activating TRPV2. Various methods of computer-based virtual screen using atomic coordinates are generally known in the art. For example, U.S. Pat. No. 5,798, 247 (which is incorporated herein by reference) discloses a method of identifying a compound (specifically, an interleukin converting enzyme inhibitor) by determining binding interactions between an organic compound and binding sites of a binding cavity within the target protein. The binding sites are defined by atomic coordinates.

The compounds designed or selected based on rational drug design or virtual screen can be tested for their ability to modulate (interfere with or strengthen) the interaction between the interacting partners within the protein complexes of the present invention. In addition, the compounds can further be tested in TRPV2 channel conductivity assays or animal models as described supra.

Following the selection of desirable compounds according to the methods disclosed above, the methods of the present invention further provide for the manufacture of the selected compounds. The compounds can be manufactured for further experimental studies, or for therapeutic use. The compounds identified in the screening methods of the present invention can be made into therapeutically or prophylactically effective drugs for preventing or ameliorating diseases, disorders or symptoms caused by or associated with TRPV2, such as pain, or inflammation, etc.

EXAMPLE 1

Expression of Rat and Human TRPV2 in HEK293 cells

A cDNA fragment encoding the full-length rat TRPV2 was subcloned into pCI-neo (Promega, Madison, Wis.) mammalian expression vector. The expression construct was then transfected into HEK293 cells with FuGene6 transfection reagent (Roche, Indianapolis, Ind.) according to the vendor's protocol. Stable cell lines were selected by growth in the presence of 400 μg/ml G418. Single G418 resistant clones were isolated and purified. Stable expression of rat TRPV2 in these cells was confirmed by Western blot analysis with an anti-rat TRPV2 specific antibody (Chemicon, Temecula, Calif.), $Ca^{2+}$ imaging assay (FLIPR) and whole cell patch clamp analyses.

A cDNA fragment encoding the full-length human TRPV2 was subcloned into pCI-neo or pcDNA3 mammalian expression vectors. The expression constructs were then transfected into HEK293 cells with FuGene6 transfection reagent (Roche, Indianapolis, Ind.) according to vendor's protocol. TRPV2-expressing HEK293 cells were cultured in DMEM supplemented with 10% fetal bovine serum, 100 units/ml penicillin, and 100 μg/ml streptomycin for 48-72 hr and either evaluated for transient expression and/or activity, or dosed with 400 μg/ml G418 to select for stably-transfected TRPV2-expressing cell clones. Cells were maintained at 37° C. and in 5% $CO_2$.

EXAMPLE 2

TRPV2 is Activated by $\Delta^9$-tetrahydrocannabinol ($\Delta^9$-THC)

To search for pharmacological activators of TRPV2, $\Delta^9$-THC, a major psychoactive constituent of marijuana derived from *Cannabis*, was tested. The rat TRPV2-expressing HEK293 cells were seeded in a 384-well plate at a concentration of $5 \times 10^3$ cells/well and incubated overnight at 37° C. The following day, the cells were loaded with buffer and calcium dye 3 (Molecular Devices, Sunnyvale, Calif.) in a final volume of 50 μl and incubated for 30 minutes at 37° C./5% $CO_2$ followed by 30 additional minutes at room temperature. The fluorescence intensity was measured by a fluorescent plate reader (FLIPR) before, during and after the addition of test compounds.

As shown in FIG. 4A, addition of 100 μM $\Delta^9$-THC solid line but not buffer (dotted line), caused a robust elevation of intracellular $Ca^{2+}$ in rat TRPV2-expressing HEK293 cells. In contrast, no significant intracellular $Ca^+$ elevation was observed in untransfected HEK293 cells at the same concentration of $\Delta^9$-THC (dashed line), suggesting that the elevation of intracellular $Ca^{2+}$ was mediated by rat TRPV2. Activation of rat TRPV2 by $\Delta^9$-THC was dose-dependent with an $EC_{50}$ value of 15.7 uM and Hill slope of 1.04 (FIG. 4B).

To further confirm the $\Delta^9$-THC effect on TRPV2, whole-cell patch clamp studies were performed. The extracellular solution contained (in mM): NaCl, 132; $CaCl_2$, 1.8; KCl, 5.4; $MgCl_2$, 0.8; HEPES, 10; glucose, 10; pH=7.4. The intracellular solution used to fill recording pipettes contained (in mM): CsCl, 145; EGTA, 5; HEPES, 10; glucose, 5; pH=7.4. Recordings were performed using the conventional whole-cell patch clamp technique, 2-3 days after transient transfection of human TRPV2 into HEK293 cell or 1-2 days after plating HEK293 cells stably expressing rat TRPV2 onto glass coverslips. Currents were amplified by a patch clamp amplifier and filtered at 2 kHz (Axopatch 200B), sampled at 10 kHz using Digidata 1322A and acquired and analyzed with pClamp 9.0 (all instruments from Molecular Devices, CA). A 600 ms voltage ramp was given once every five seconds from −100 mV to +60 mV. The holding potential between voltage ramps was −100 mV. Extracellular solutions were applied to the cell at 0.5 ml/min via a gravity-fed perfusion system. All experiments were performed at 22° C.

As shown in FIG. 5B, upon application of 100 μM $\Delta^9$-THC, there was a significant increase of the whole-cell current amplitude (gray solid line) in HEK293 cells expressing rTRPV2 compared to control (black dotted line) at both hyperpolarized and depolarized membrane potentials. However, this effect was more pronounced at depolarized potentials. The same concentration of $\Delta^9$-THC elicited no current above control level in untransfected HEK293 cells (data not shown). The $\Delta^9$-THC-activated current had a reversal potential near 0 mV, indicating the relatively unselective (at least for the cations used in these experiments) nature of the channel. Similar effects induced by $\Delta^9$-THC were also observed in human TRPV2 (FIG. 5A). Furthermore, the $\Delta^9$-THC-activated currents were significantly inhibited by 10 μM ruthenium red (RR), a non-selective TRP channel inhibitor (black line) in both rat and human TRPV2. Taken together, these results indicate that $\Delta^9$-THC activates currents mediated by TRPV2 in these cells.

EXAMPLE 3

TRPV2 is Activated by Other Cannabinoids

To further explore activation of TRPV2 by cannabinoids, several different classes of cannabinoids were tested in a FLIPR calcium mobilization assay using 100 μM compound concentrations (except for anandamide which was at 120 μM) as evaluated using rat TRPV2-expressing HEK293 cells. All data was normalized to that observed for 100 μM $\Delta^9$-THC. The tested compounds included: the non-psychoactive constituents of marijuana (cannabidiol and cannabinol); synthetic analogs of THC (nabilone, CP 55,940, HU210, HU211, HU-308, HU331, 11-hydroxy-Δ9-THC, and O-1821); several endocannabinoids (anandamide, 2-arachidonoyl-glycerol (2-AG) and their analog palmitoylethanolamide (PEA)); a cannabinoid transport blocker (AM404); other synthetic cannabinoid receptor agonists (WIN55,212-2, WIN55,212-3, JWH015, JWH133, O-1918 and CAY10429); and the non-selective agonist, 2-APB The ability of these compounds to activate rat TRPV2 is shown in Table 1. The data suggest that TRPV2 could be activated by more than one class of cannabinoids.

TABLE 1

Activation of rat TRPV2 by Cannabinoids

| Compound | Compound Structure | % Response | $EC_{50}$ |
|---|---|---|---|
| $\Delta^9$-THC | 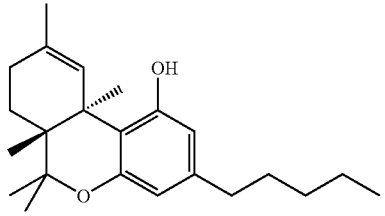 | 100 | 15.5 uM |
| Cannabinol | 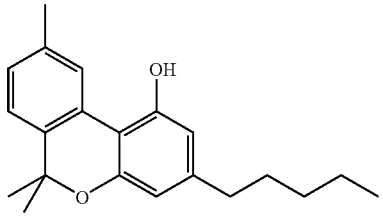 | 68 | 77.7 uM |
| Nabilone | 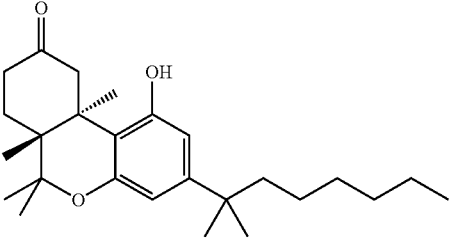 | 59 | |
| CP55,940 | 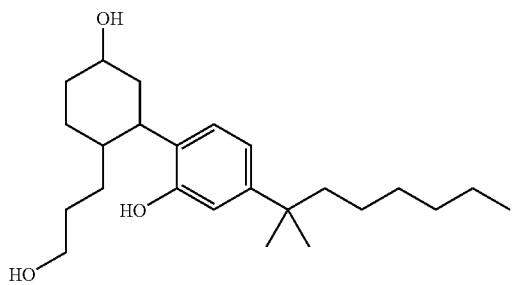 | 43 | |
| HU-210 | 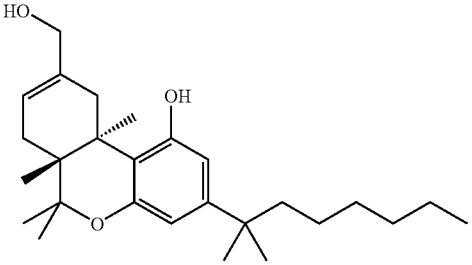 | 39 | |

TABLE 1-continued

Activation of rat TRPV2 by Cannabinoids

| Compound | Compound Structure | % Response | $EC_{50}$ |
| --- | --- | --- | --- |
| WIN-55,212-2 | 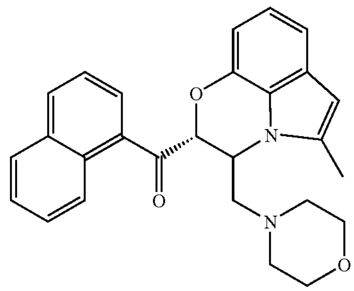 | −2 | |
| JWH015 | 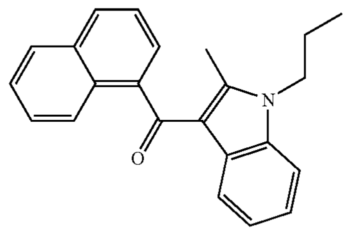 | 14 | |
| Anandamide | 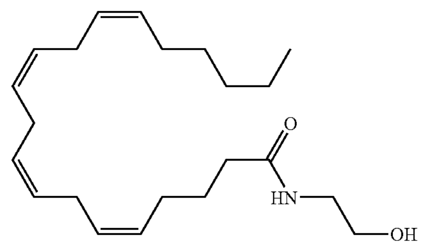 | 0 | |
| 2-AG | 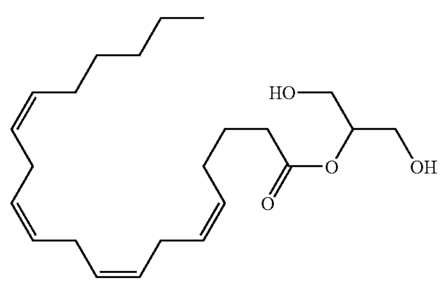 | 30 | |
| PEA | 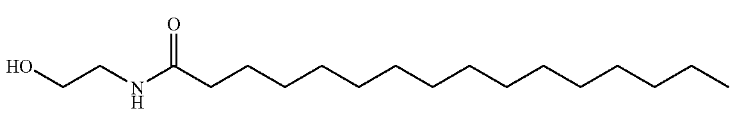 | 5 | |
| AM404 | 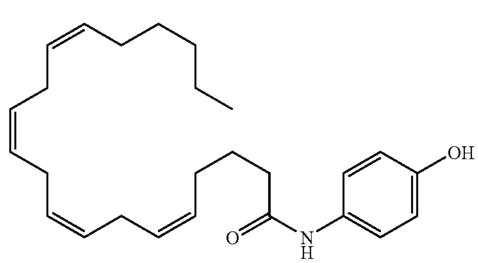 | 6 | |

TABLE 1-continued

Activation of rat TRPV2 by Cannabinoids

| Compound | Compound Structure | % Response | $EC_{50}$ |
|---|---|---|---|
| Cannabidiol | 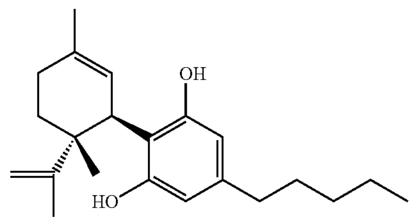 | 163 | 3.7 uM |
| 11-hydroxy-$\Delta^9$-THC | 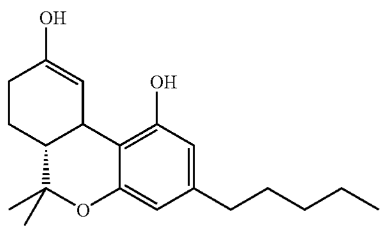 | 58 | |
| O-1821 | 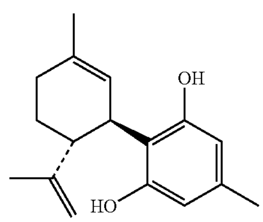 | 95 | ~20 uM |
| O-1918 | 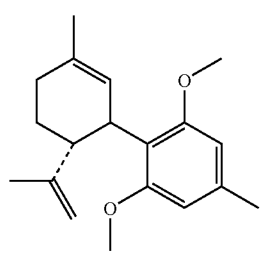 | 6 | |
| CAY10429 | 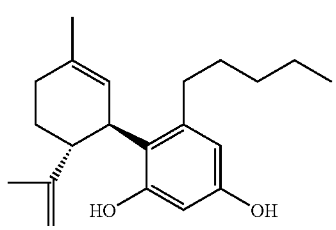 | 0 | |
| WIN 55,212-3 | 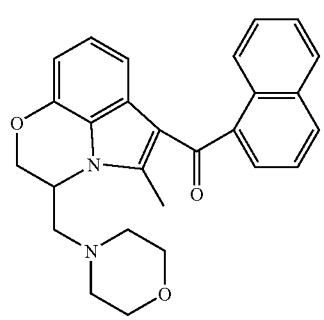 | 7 | |

TABLE 1-continued
Activation of rat TRPV2 by Cannabinoids
| Compound | Compound Structure | % Response | EC$_{50}$ |
|---|---|---|---|
| HU-211 | 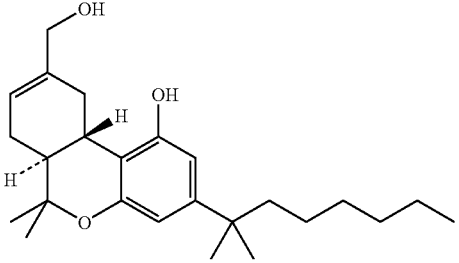 | 31 | |
| HU-308 | 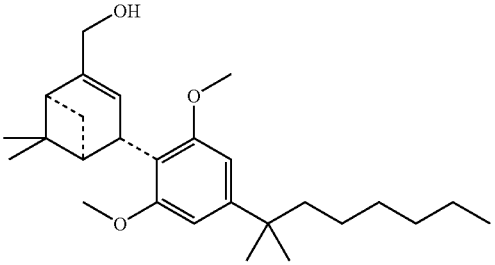 | 10 | |
| HU-331 | 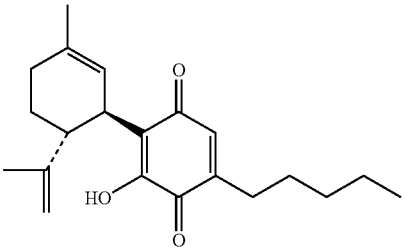 | 47 | ~14 uM |
| JWH-133 | 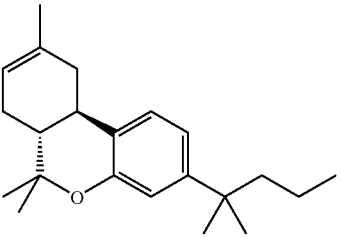 | 5 | |
| 2-APB | 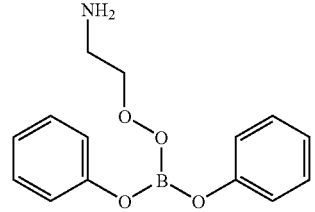 | 102 | 8.0 uM |

EXAMPLE 4

Δ⁹-THC Selectively Activates TRPV2

A selected number of cannabinoids were also tested against HEK293 cells expressing human TRPV1 and canine TRPM8 in the FLIRP assay. As summarized in Table 2, Δ⁹-THC (240 μM) and cannabinol (600 μM) showed no significant activation of TRPV1, whereas anandamide, 2-AG and AM404 activated TRPV1, consistent with previous reports. None of these cannabinoids showed agonist effect against TRPM8.

|  | TRPV1 | TRPV2 | TRPM8 |
| --- | --- | --- | --- |
| Δ⁹-THC (240 μM) | − | + | − |
| Cannabinol (600 μM) | − | + | − |
| Anandamide (120 μM) | + | − | − |
| 2-AG (120 μM) | + | + | − |
| AM404 (120 μM) | + | − | − |

EXAMPLE 5

Deletion Mutants of TRPV2 Were Activated by Cannabinoids

TRPV2 deletion mutants were constructed and tested for activation by Δ⁹-THC, 2-APB and high temperature stimulation. Methods of this Example can be used to construct and test any type of TRPV2 deletion mutants, including, but not limited to, mutants having one or more amino acid residues deleted at the N-terminal of the TRPV2, at the C-terminal of the TRPV2, and/or at any other location of the TRPV2.

DNA molecules encoding the deletion mutants were amplified by PCR using the rat TRPV2 cDNA as the template. For amino-terminal deletions, a series N-terminal forward primers encoding an initiating methionine in frame with sequences matching adjacent regions of the desired start at residues G21 (mutant N20, SEQ ID NO:11), P33 (N32, SEQ ID NO:12), A66 (N65, SEQ ID NO:13) and V84 (N83, SEQ ID NO:14) paired with a C-terminal reverse primer were used for PCR amplification. While for carboxyl-terminal deletions, a forward N-terminal primer paired with a series C-terminal reverse primers ending at residues R706 (C51, SEQ ID NO:7), P729 (C32, SEQ ID NO:8), P738 (C23, SEQ ID NO:9) and E750 (C11, SEQ ID NO:10) with an in-frame stop codon at the terminal end of the open reading frame were used for amplification. After PCR amplification and purification, the DNA molecules encoding the deletion mutants were subcloned into the pCI-neo mammalian expression vector and the constructs were confirmed by DNA sequencing. The DNA molecules that encoded for the various TRPV2-deletion mutants comprised the nucleotide sequences of: SEQ ID NO:18 (N20), SEQ ID NO:19 (N32), SEQ ID NO:20 (N65), SEQ ID NO:21 (N83), SEQ ID NO:22 (C51), SEQ ID NO:23 (C32), SEQ ID NO:24 (C23), and SEQ ID NO:25 (C11).

The deletion mutant constructs were then transfected into HEK293 cells using Fugene 6 reagent (Roche) as per the manufacturer's instructions. At 24 hours post-transfection, the cells were harvested and replated in fresh DMEM medium supplemented with 10% fetal bovine serum, 100 units/ml penicillin, and 100 μg/ml streptomycin. The cells were distributed onto poly-D-Lysine coated 96-or 384- well plates at a density of approximately 40,000 and 10,000 cells per well, respectively. At approximately 48 hours post-transfection, the medium was removed from the assay plate and replaced with Calcium 3 Dye Buffer (Molecular Devices) using the protocol available from the manufacturer. Calcium mobilization was triggered using Δ⁹-THC or 2-APB or elevated temperature buffer and measured using either FLIPR or FLEX STATION instruments.

It was found that deletion mutants of rat TRPV2 lacking the N-terminal 20, 33, 66, or lacking the C-terminal 11, 23, or 32 amino acid residues were still active in their responses to Δ⁹-THC (FIG. 6), 2-APB and an elevated temperature of about 53° C. (data not shown).

EXAMPLE 6

Activation of TRPV2 Chimera

The domain-swapping chimeras between rat and human TRPV2s were also made and tested for activation by Δ⁹-THC, 2-APB and high temperature stimulation. Methods of this Example can be used to construct and test any type of TRPV2 chimeras, including, but not limited to, the domain-swapping chimeras between TRPV2s from different animals, and the chimeras between TRPV2 and other TRPV channels such as TRPV1 and TRPV3.

Based on the predicted topology and primary sequence features of TRPV2, TRPV2 are divided into 3 major domains: 1) the amino-terminal intracellular domain; 2) the transmembrane domain; and 3) the carboxyl-terminal intracellular domain. For a chimera, each domain can be of rat (R) or human (H) origin. Three rat and human TRPV2 chimera were constructed and tested herein. RRH (SEQ ID NO:15) was a chimera comprising rat 1-392 aa, rat 393-646 aa, and human 647-764 aa. RHR (SEQ ID NO:16) was a chimera comprising rat 1-392, human 391-646, and rat 647-761. HRR (SEQ ID NO:17) was a chimera comprising human 1-390, rat 393-646, and rat 647-761.

DNA molecules encoding the three rat and human TRPV2 chimeras were obtained by fusion PCR. First, DNA molecules encoding the desired TRPV2 domains were amplified by PCR using the rat or human TRPV2 cDNA as the template with synthetic primer DNA containing in-frame sequence that overlapped with the other species domain to be linked. After PCR amplification and purification, DNA molecules encoding the desired TRPV2 domains from human and rat were combined and used as templates for fusion PCR with primer DNA matching the 5' and 3' end sequences of the coding sequence for the full length TRPV2 chimera. The DNA molecules that encoded the various TRPV2 chimeras comprised the nucleotide sequences of: SEQ ID NO: 26(RRH), SEQ ID NO:27 (RHR), and SEQ ID NO:28 (HRR).

The DNA molecules encoding the TRPV2 chimera were then subcloned into the mammalian expression vector, pCI-neo and the resulting constructs confirmed by DNA sequencing. The chimeras were transiently expressed in HEK293 cells and their responses to a variety of stimulators were also tested as described in Example 5.

Chimera RHR was fully responsive to the addition of Δ⁹-THC (FIG. 7A),). Although the HEK cells expressing chimera RRH or HRR separately were poorly, or not active, respectively, the cells co-expressing both chimeras (RRH+HHR) were fully responsive to Δ⁹-THC (FIG. 7B. Similar responses by the above-listed chimeras to 2-APB stimulation were observed (data not shown). The gain of function study by coexpression of two inactive mutants suggests that a functional TRPV2 channel is a complex with multiple subunits and some of the critical functional domains act in trans rather than in cis.

What is claimed is:

1. A method of identifying a compound that decreases the biological activity of TRPV2, comprising the steps of:
   a. contacting a TRPV2 polypeptide with a cannabinoid that is capable of activating the TRPV2 activity under a condition in which the TRPV2 is activated by the cannabinoid, wherein said TRPV2 polypeptide comprises a sequence selected from the group consisting of SEQ ID NO:2, a sequence having greater than about 70% amino acid sequence identity to SEQ ID NO:2, a functional fragment of SEQ ID NO:2 wherein said functional fragment of SEQ ID NO: 2 maintaining the biological activity of TRPV2 and comprising amino acids 66 to 729 of SEQ ID NO:2, a sequence having greater than about 70% amino acid sequence identity to said functional fragment of SEQ ID NO:2, a deletion or modification of SEQ ID NO:2 that maintains said functional fragment of TRPV2, and a sequence having greater than 70% amino acid sequence identity to a deletion or modification of SEQ ID NO:2 that maintains said functional fragment of TRPV2;
   b. contacting the TRPV2 polypeptide with a test compound;
   c. measuring the biological activity of the TRPV2 in the presence of both the cannabinoid and the test compound;
   d. repeating step a);
   e. measuring the biological activity of the TRPV2 in the presence of the cannabinoid but not the test compound; and
   f. comparing the TRPV2 activity measured from step c) with that from step e); thereby identifying the compound that decreases the biological activity of TRPV2 when the TRPV2 activity measured from step c) is less than that from step e).

2. The method of claim 1, wherein step a) is performed prior to step b).

3. The method of claim 1, wherein step a) is performed after step b).

4. The method of claim 1, wherein steps a) and b) are performed simultaneously.

5. The method of claim 1, wherein the TRPV2 is associated with an isolated membrane.

6. The method of claim 1, wherein the TRPV2 is present in a cell.

7. The method of claim 6, wherein the cell is a neuron.

8. The method of claim 7, wherein the neuron is a dorsal root ganglia neuron.

9. The method of claim 1, wherein the TRPV2 has an amino acid sequence of SEQ ID NO: 2, SEQ ID NO: 4, SEQ ID NO: 6, SEQ ID NO: 8, SEQ ID NO: 9, SEQ ID NO:10, SEQ ID NO:11, SEQ ID NO:12, SEQ ID NO:13, or SEQ ID NO:16.

10. The method of claim 1, wherein the TRPV2 is recombinantly expressed from a cell that contains an expression vector for the TRPV2 gene.

11. The method of claim 10, wherein the expression vector comprises the nucleotide sequence that encodes a TRPV2 having an amino acid sequence of SEQ ID NO: 2, SEQ ID NO: 4, SEQ ID NO: 6, SEQ ID NO: 8, SEQ ID NO: 9, SEQ ID NO:10, SEQ ID NO:11, SEQ ID NO:12, SEQ ID NO:13, or SEQ ID NO:16.

12. The method of claim 1, wherein the biological activity of the TRPV2 is measured as calcium-influx into a cell expressing the TRPV2.

13. The method of claim 1, wherein the biological activity of the TRPV2 is measured by a method of patch clamp.

14. The method of claim 1, wherein the biological activity of the TRPV2 is measured by a CA mobilization assay.

15. The method of claim 1, wherein the biological activity of the TRPV2 is measured as its binding affinity to the cannabinoid that is capable of activating the TRPV2 activity.

16. The method of claim 1, wherein the cannabinoid is selected from the group consisting of $\Delta^9$-tetrahydrocannabinol, 11-hydroxy-$\Delta^9$-tetrahydrocannabinol, cannabinol, cannabidiol, O-1821, nabilone, CP55940, 2-AG, and HU210, HU211, HU308, and HU331.

17. The method of claim 1, further comprising the step of determining the extent to which the test alters the biological activity of TRPV2 at an activation temperature for TRPV2.

18. The method of claim 1, further comprising the steps of
   a. administering the test compound to an animal; and
   b. determining the extent to which the test compound alters the nociceptive response of the animal.

* * * * *